United States Patent
Murray

(10) Patent No.: US 6,562,626 B1
(45) Date of Patent: *May 13, 2003

(54) METHOD FOR MONITORING TEXTILE FIBER QUALITY, AND FOR ANALYSIS AND IDENTIFICATION OF PAPER, WOOD AND OTHER CELLULOSE CONTAINING MATERIALS

(76) Inventor: Allen K. Murray, 17935 Sky Park Cir., Suite E, Irvine, CA (US) 92614-6321

( * ) Notice: Subject to any disclaimer, the term of this patent is extended or adjusted under 35 U.S.C. 154(b) by 0 days.

This patent is subject to a terminal disclaimer.

(21) Appl. No.: 09/427,654

(22) Filed: Oct. 27, 1999

Related U.S. Application Data

(63) Continuation-in-part of application No. PCT/US99/00368, filed on Jan. 7, 1999, which is a continuation-in-part of application No. 09/003,679, filed on Jan. 7, 1998, now Pat. No. 6,051,435, which is a continuation-in-part of application No. 08/516,953, filed on Aug. 18, 1995, now Pat. No. 5,710,047.

(60) Provisional application No. 60/096,162, filed on Aug. 11, 1998, and provisional application No. 60/106,001, filed on Oct. 28, 1998.

(51) Int. Cl.$^7$ .............................................. G01N 33/68

(52) U.S. Cl. .............................. 436/94; 436/174; 47/58

(58) Field of Search .......................... 436/94, 174, 161; 47/58

(56) References Cited

U.S. PATENT DOCUMENTS 6,051,435 A * 4/2000 Murray ........................ 436/94
6,210,801 B1 * 4/2001 Lou et al. .................... 428/393

* cited by examiner

*Primary Examiner*—Lyle A. Alexander
(74) *Attorney, Agent, or Firm*—Crosby, Heafey, Roach & May

(57) ABSTRACT

A method of analyzing cell wall components based on a hot dilute acid extraction of plant cellulosic materials such as cotton fibers or wood pulp. The extracts are analyzed by high pH anion exchange chromatography to separate and characterize the carbohydrates. This method extracts a characteristic series of carbohydrate multimers containing galactose, mannose and glucose. The pattern of multimers is indicative of origin of the cellulosic material (e.g., the plant species the material comes from) as well as quality and processing state of the material. That is, in textiles lack of multimers is indicative of textile wear and can be used to determine which manufacturing treatment will improve fabric life. In addition the multimers are shown to contain a protein component. Chemical agents that cross-link the protein component alter the extractability of the multimers and can be used to alter favorably the resistance of fabric to washing induced wear. In the case of wood products unique multimer patterns can be used to identify the plant species producing the wood. Selective disruption of the linkages of the multimers to cellulose can be used to produce high purity cellulose.

5 Claims, 40 Drawing Sheets

METHOD FOR MONITORING TEXTILE FIBER QUALITY, AND FOR ANALYSIS AND IDENTIFICATION OF PAPER, WOOD AND OTHER CELLULOSE CONTAINING MATERIALS

The present application is a Continuation In Part of: application Ser. No. 09/003,679, filed Jan. 7, 1998, now U.S. Pat. No. 6,051,435 which is a Continuation In Part of application Ser. No. 08/516,953, filed on Aug. 18, 1995, now issued as U.S. Pat. No. 5,710,047, Jan. 20, 1998; of U.S. Provisional 60/096,162, filed Aug. 11, 1998; and of U.S. Provisional Patent No. 60/106001, filed Oct. 28, 1998, and International Application No. PCT/US99/00368, filed Jan. 7, 1999, of all of which are hereby incorporated by reference into this application.

BACKGROUND OF THE INVENTION

1. Field of the Invention

This invention concerns a method of monitoring precursor pools for cell wall biosynthesis and using them to identify the origins of various plant cell walls. In particular this application describes biochemical methods of assessing the quality of cotton fibers and of "fingerprinting" wood samples.

2. Description of Related Art

In the parents of this application the present inventor described his surprising discovery that it is possible to extract a carbohydrate-containing fraction from properly prepared plant material by a simple cold water process. Essentially, plant tissue is prepared by rapid freezing (preferably by use of liquid nitrogen or solid carbon dioxide) and is then lyophilized and stored at temperatures below freezing. As disclosed in the above-referenced parent applications carbohydrate-containing cell wall fractions can be easily extracted from the lyophilized tissue by cold aqueous extraction; then, special techniques of High Pressure Liquid Chromatography (HPLC) allow resolution of the aqueous extract into constituent mono and polysaccharides which can be further hydrolyzed to identify the constituent monosaccharides.

The use of high pH anion exchange chromatography with pulsed amperometric detection (HPAEC-PAD) makes possible the unambiguous identification of cell wall constituents. In HPAEC a salt gradient (such as a sodium acetate gradient) is applied to a column of special ion exchange resins held at a high pH to sequentially elute various mono and polysaccharides. Essentially, the hydroxyl groups of the sugars act as extremely weak acids that become deprotonated at the high pH, binding to the ion exchange matrix until eluted by the gradient.

While there are a number of vendors of HPAEC materials, the current invention has employed products and systems produced by the Dionex Corporation of Sunnyvale, Calif. These products and systems are explained in full in the Dionex Technical Notes, particularly in Technical Notes 20 and 21, which are hereby incorporated into this application. The carbohydrate fractions isolated from plant cell walls were analyzed using Dionex CarboPac PA-1 and PA-100 columns. Both of these columns contain poly-styrene/divinylbenzene cross-linked latex microbeads (350 nm diameter) with quaternary amine functional groups. The columns were operated under the manufacturer's recommended pressure conditions (4000 psi maximum) in sodium hydroxide eluted with a sodium acetate elution gradient. When necessary, sugar alcohols were analyzed using a CarboPac MA1 column that contains porous beads (8.5 $\mu$m diameter) of vinylbenzene chloride/divinylbenzene with alkyl quaternary ammonium functional groups The polysaccharides analyzed in the present invention are appropriately referred to as "glycoconjugates" because they comprise a monosaccharide conjugated to at least one additional monosaccharide (i.e., to form an oligo or polysaccharide) and optionally to a protein or a lipid. As will be disclosed below at least some of the glycoconjugates comprise polysaccharides conjugated to a protein moiety. To summarize, glycoconjugates may be polysaccharides, polysaccharides containing a protein moiety, polysaccharides containing a lipid moiety and/or any combination of these. In the present application only polysaccharides and polysaccharides containing a protein moiety have been unambiguously identified. In any case HPAEC characterizes the polysaccharide component of the glycoconjugate.

BRIEF DESCRIPTION OF THE DRAWINGS

The objects and features of the present invention, which are believed to be novel, are set forth with particularity in the appended claims. The present invention, both as to its organization and manner of operation, together with further objects and advantages, may best be understood by reference to the following description, taken in connection with the accompanying drawings.

DETAILED DESCRIPTION OF THE PREFERRED EMBODIMENTS

The following description is provided to enable any person skilled in the art to make and use the invention and sets forth the best modes contemplated by the inventor of carrying out his invention. Various modifications, however, will remain readily apparent to those skilled in the art, since the general principles of the present invention have been defined herein specifically to provide methods for determining identity and quality of plant cell wall materials, especially cotton fibers, and other cellulose containing products, such as wood and paper, through the analysis of selected polysaccharide fractions.

Acid Extractable Multimers

Figure 1:
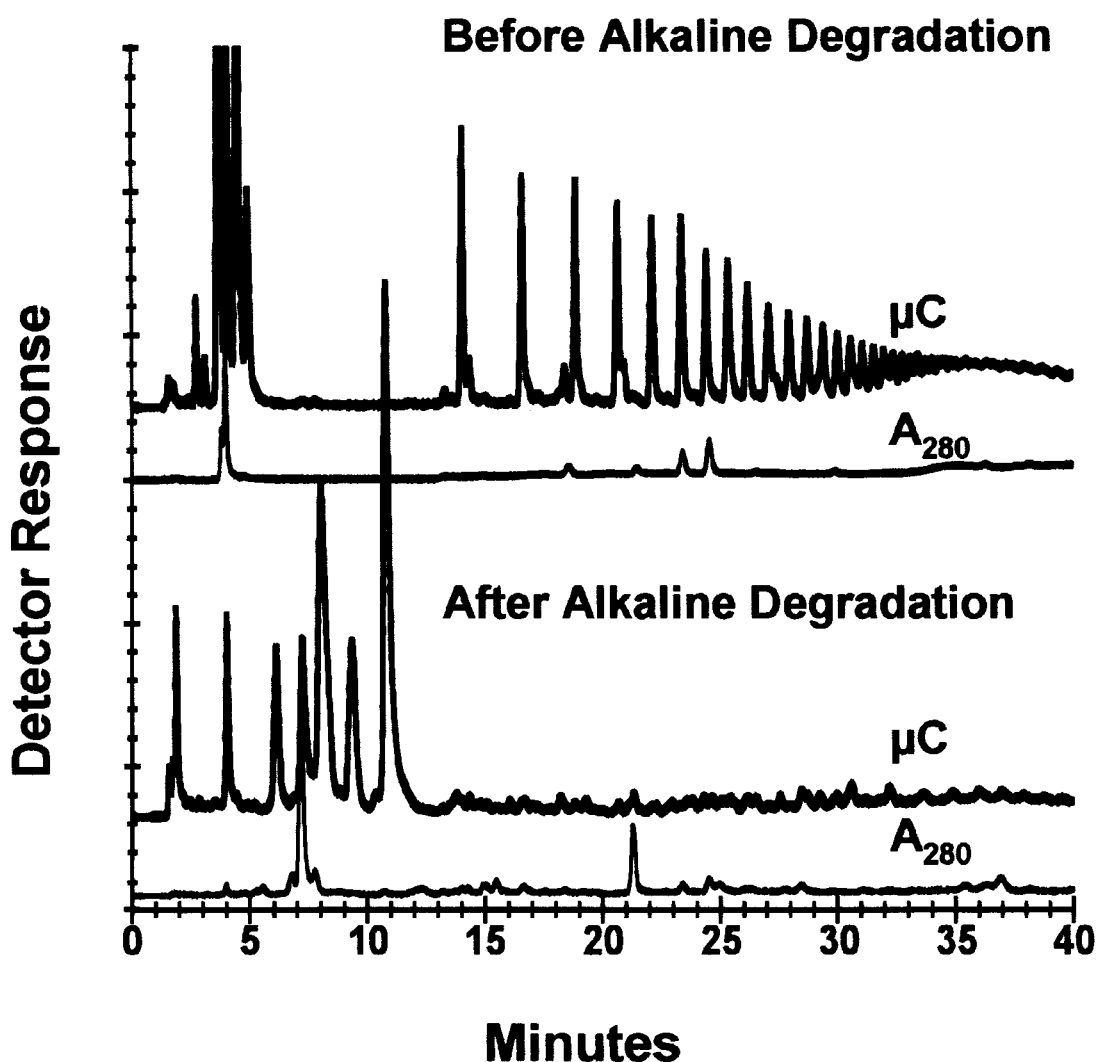
FIG. 1 shows an alkaline degradation experiment on multimers extracted from plant tissues according to the present invention.
Figure 2:
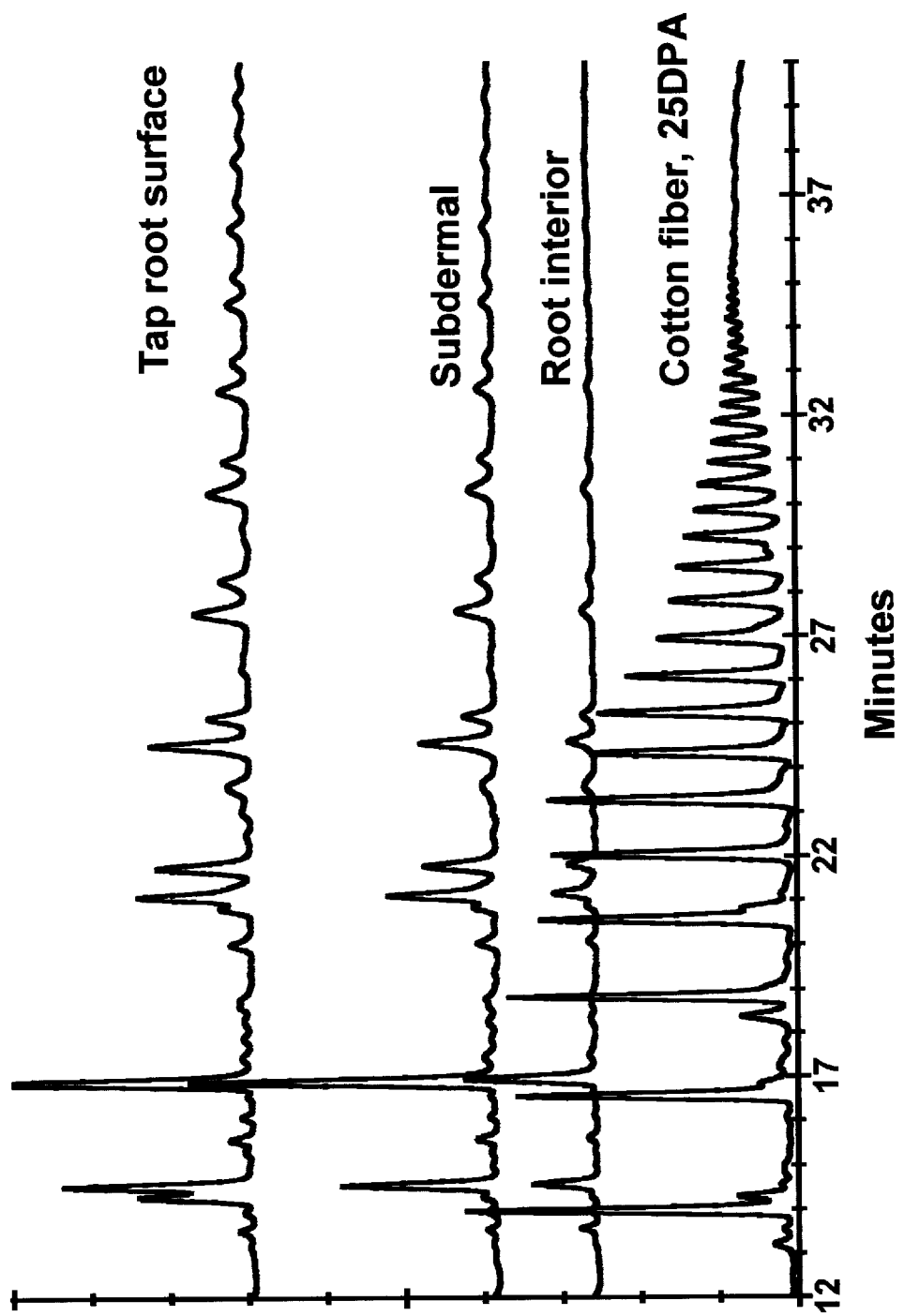
FIG. 2 compares multimers extracted from a normal cotton fiber with multimers extracted from portions of sugar beet root to demonstrate that some of these carbohydrates are found in cell walls of widely divergent plants; here the multimers from each zone are the same but their abundance is increased in tissues with a higher degree of organization.

Perhaps the most exciting and unexpected discovery of the present research was the finding that following the aqueous extraction it is possible to extract a multimer fraction by boiling for 30 minutes in dilute 0.1M HCl. Presumably these multimers represent some component that connects the paracrystalline cellulose in the wall. Like the GC-2 (discussed in the parent applications) compounds the multimers are reducing sugars indicating a non-typical glycan linkage in the polymers (see FIG. 1). Hydrolysis (alkaline) of individual peaks has shown that they contain galactose, glucose and mannose. In classical plant cell wall research dilute mineral acids are sometime used to extract pectins or "pectic materials" which, by definition, contain galacturonic acid residues. Clearly, the multimers are not pectins or pectic materials. Further, it is necessary to first perform the cold aqueous extraction so that the multimers are not obscured by the GC-1 and GC-2 compounds. Further analysis of the multimers of normal fibers has revealed that the major difference between successive multimers is in addition of glucose units. That is, successive multimers in a series have comparable amounts of galactose and mannose but different amounts of glucose. It appears certain that many of these same multimers are found in a variety of cell walls. FIG. 2 shows that HCl extracts of sugar beet root tissue contains a multimer series wherein several of the compounds exactly overlap some of the cotton multimers.

Figure 3:
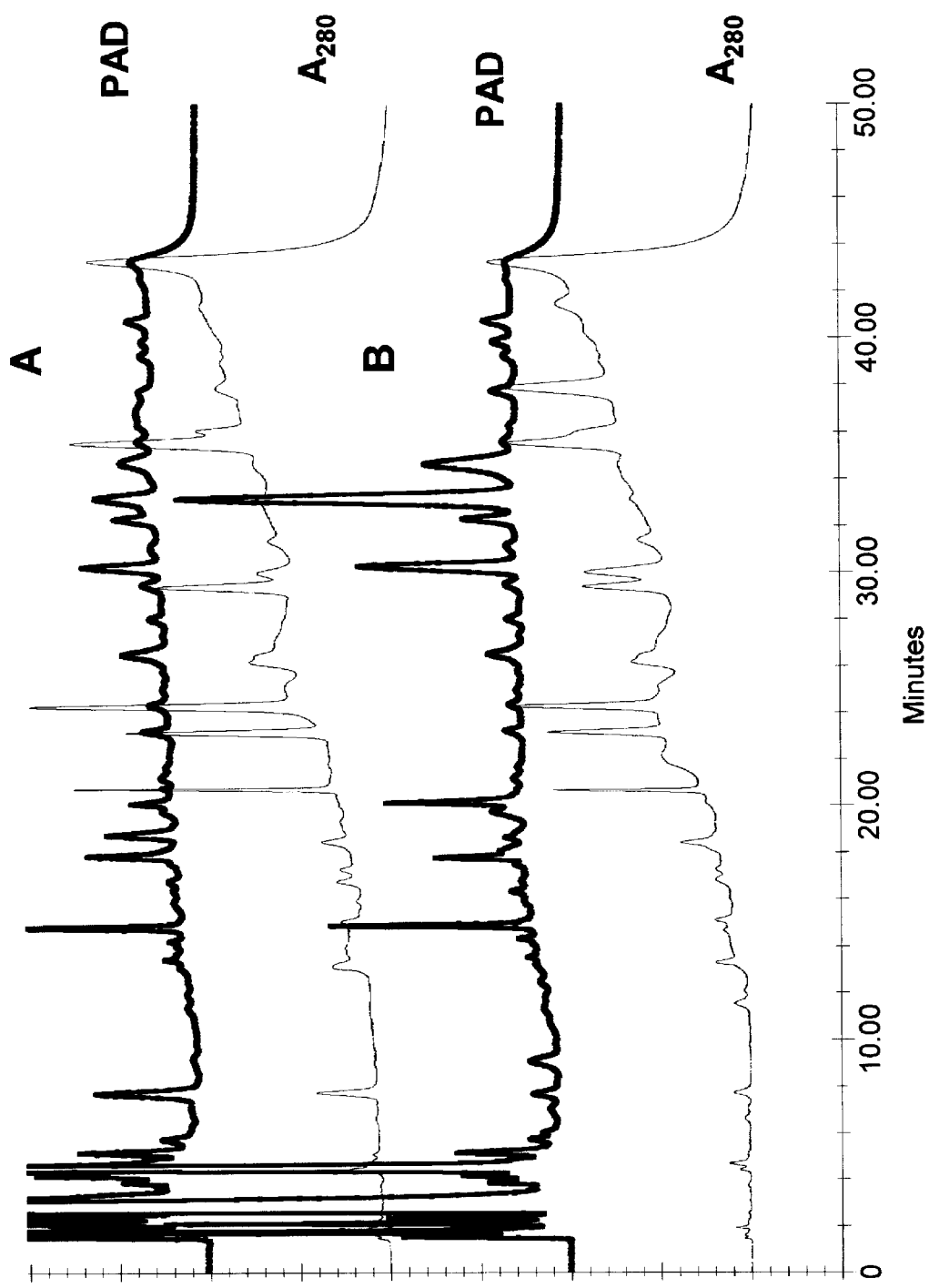
FIG. 3 shows multimers extracted from a) a marine alga (Macrocystis sp.) compared with those extracted from b) a marine flowering plant (Zostera sp.).

It would appear that the multimers revealed by the method of the present invention are indeed a "universal" feature of plant cell walls. A prime example can be seen in FIG. 3 which compares a brown alga seaweed (a kelp) Macrocystis with a marine flowering plant eelgrass—Zostera. Despite the great evolutionary distances that separate these organisms they display marked similarities in cell wall content.

Figure 4:
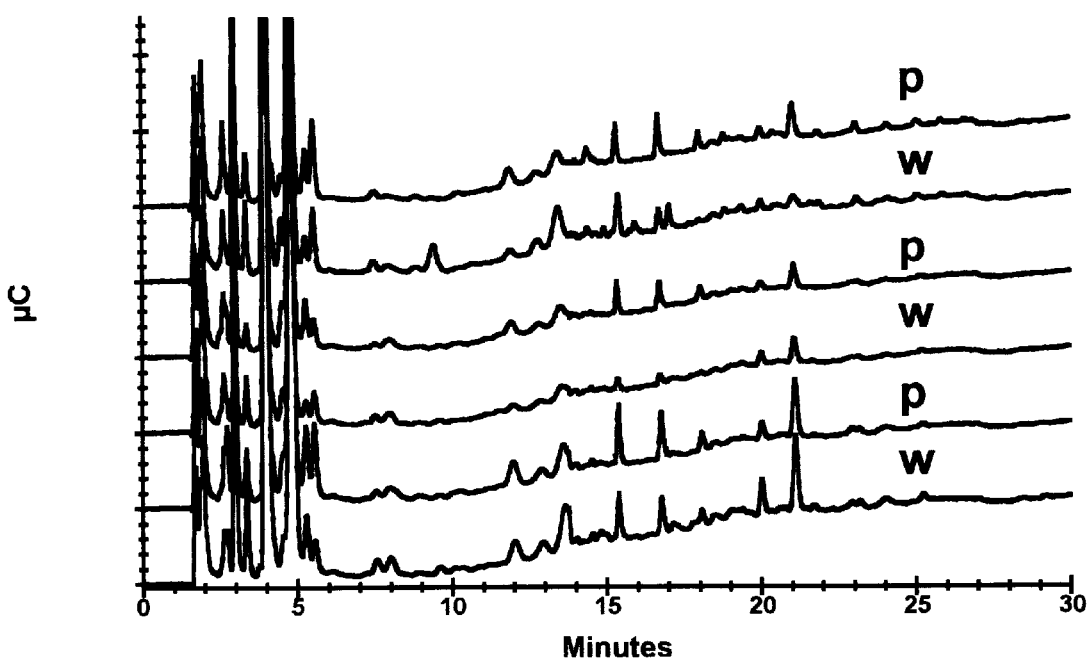
FIG. 4 shows multimers extracted from normal (p) and abnormal "white speck" (w) fibers.
Figure 5:
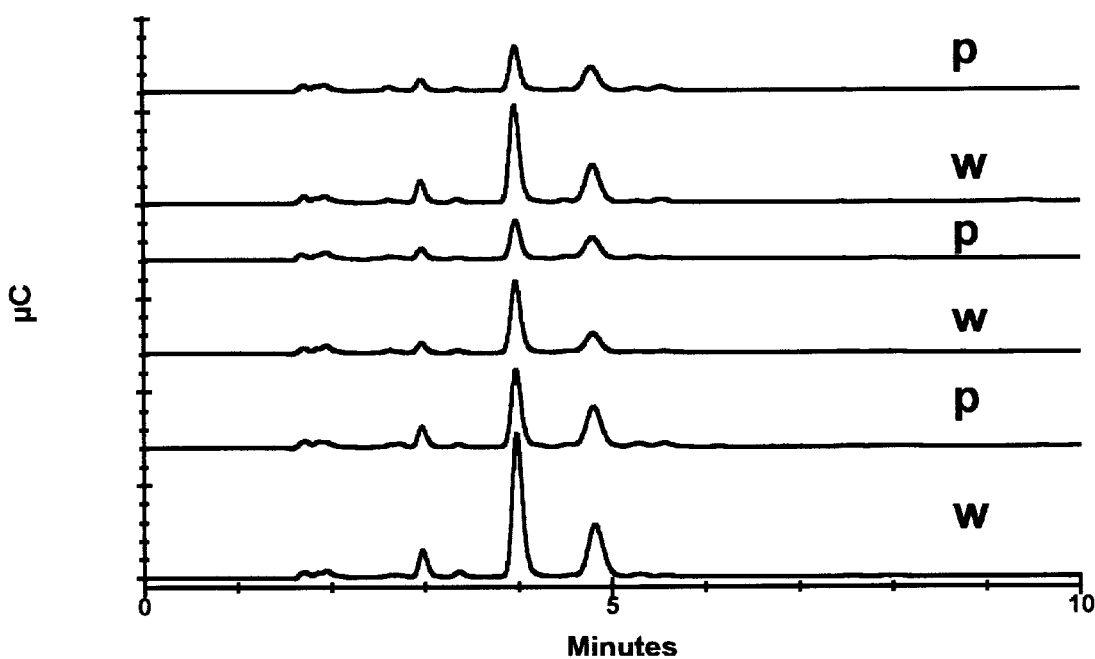
FIG. 5 shows an enlarged view of the multimer profile from FIG. 12 showing that the white speck (w) fibers have increased arabinose (ara) over the normal (p) fibers.

The multimer (oligomer) extraction is ideally suited for evaluating cotton fiber samples for a number of defects that plague the textile industry. Motes are immature, short fibers that lower the quality of cotton. Although their presence can be assessed by microscopic inspection of fibers, they also give a unique carbohydrate pattern allowing determination of mote contamination from bulk samples. Of even more importance is the presence of "white speck" fibers that are abnormal fibers that do not take up dye normally. Although this defect can be assessed by dying and inspecting the fibers, analysis of HCl multimers provides a ready way of assessing the presence of white speck fibers. As shown in FIG. 4 and FIG. 5 individual white speck (w) HCl extracts show significantly higher arabinose to glucose ratio than do the extract (p) of normal fibers.

Figure 6:
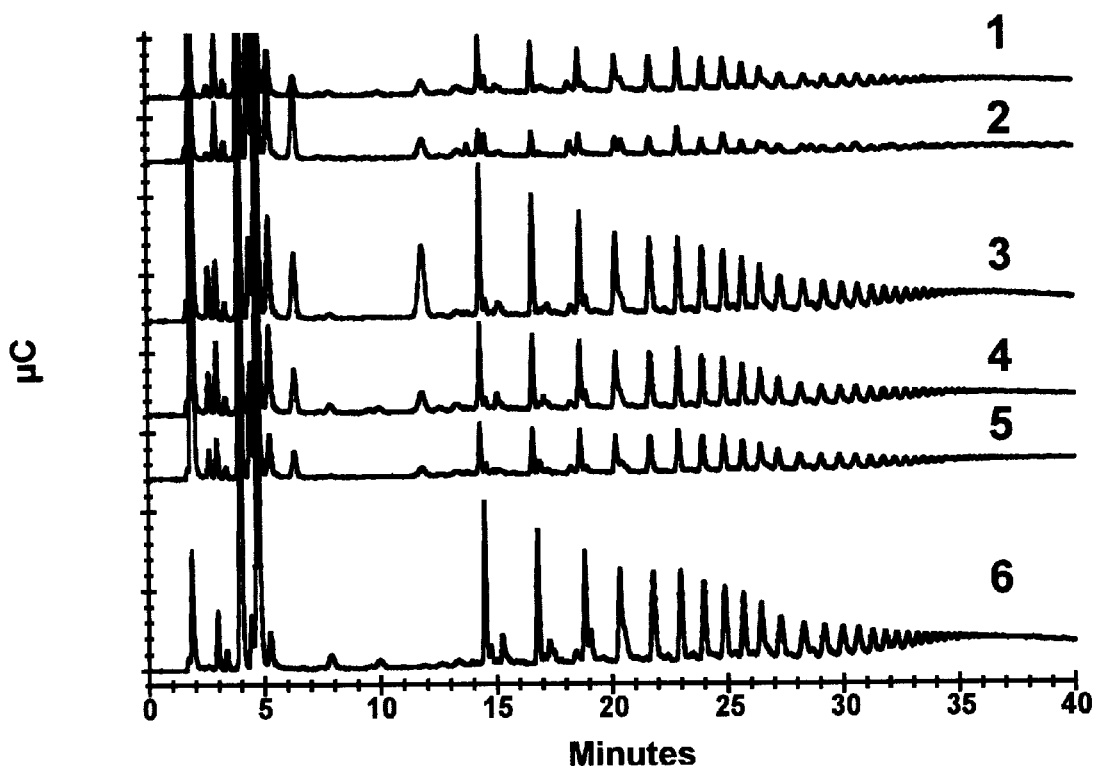
FIG. 6 shows the multimers extracted from normal fibers after incubation with a number of different substrate combinations (identified in Table 1).
Figure 6:
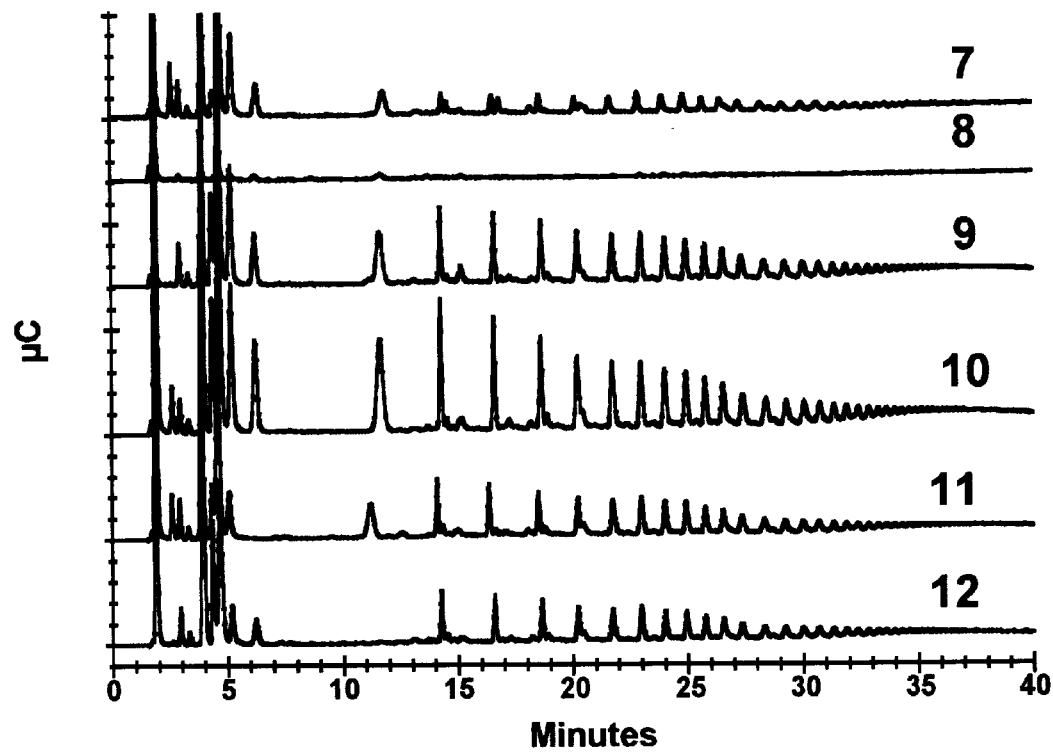

Interestingly, aqueous extracts of fibers from extremely drought-stressed plants show some of the multimers. Preliminary experiments have indicated that these multimers are similar if not identical to those released by the dilute HCl treatment. The real question is why they are released by a simple aqueous treatment. One can hypothesize that the multimers are part of a hemicellulosic "glue" that holds the cell wall cellulose microfibrils together. Under drought stress conditions carbohydrate concentrations and/or enzymatic alterations prevent the proper assembly of the cell wall components. In such a case the may not stick properly and may be easily washed out of the walls. As will be demonstrated below, there are proteins associated with at least some of the multimers (producing a special glycoconjugate). These proteins may well be responsible for some of linkages that bind the multimers in the wall. Certainly, the mild HCl extraction could be adequate to partially denature the proteins and negate their purported binding. FIG. 6 shows the multimers extracted from fibers incubated with the substrates shown in Table 1. The numeral associated with the particular trace relates to the substrates added. The important point is that the addition of certain substrate combinations (note traces 2 and 8, for example) appear to reduce the extraction of multimers. The control (addition of no exogenous substrates) displays the normal extractability of the multimers. Presumably certain substrate combinations act with endogenous enzymes to produce a more tightly cross-linked product so that fewer multimer molecules can be readily extracted.

TABLE 1

| Trace # | Glycerol mM | Sucrose mM | Raffinose mM | Cellobiose mM | Inositol mM |
|---|---|---|---|---|---|
| 1 | 684 | 20 | 20 | 20 | 20 |
| 2 | 684 | 20 | 40 | 20 | 20 |
| 3 | 684 | 20 | 20 | 40 | 20 |
| 4 | 684 | 0 | 20 | 20 | 20 |
| 5 | 684 | 0 | 20 | 20 | 40 |
| 6 | 0 | 0 | 0 | 0 | 0 |
| 7 | 684 | 20 | 20 | 40 | 0 |
| 8 | 0 | 20 | 20 | 40 | 20 |
| 9 | 0 | 20 | 20 | 40 | 0 |
| 10 | 684 | 20 | 20 | 40 | 40 |
| 11 | 684 | 20 | 0 | 40 | 20 |
| 12 | 684 | 20 | 40 | 0 | 20 |

Figure 7:
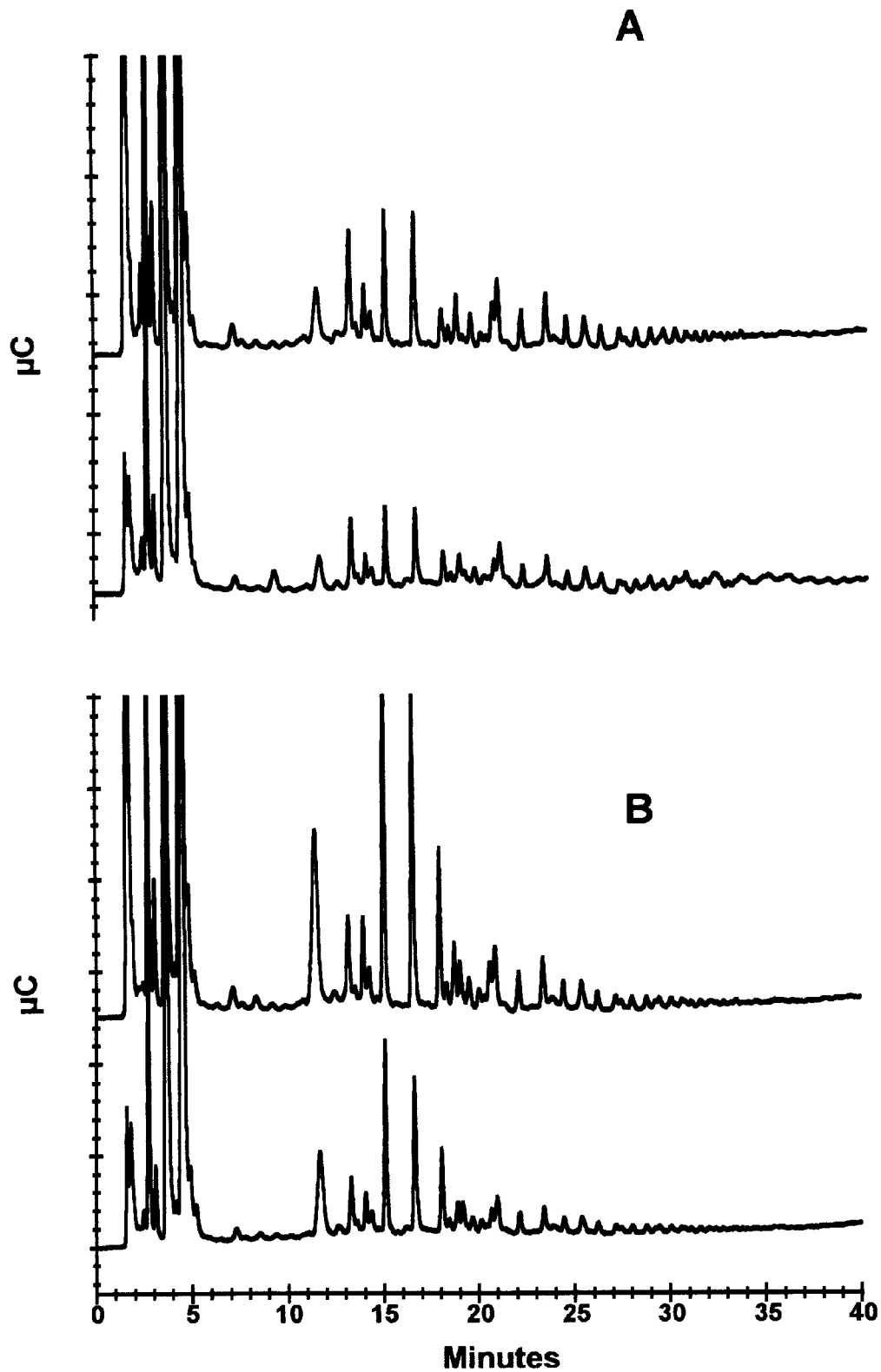
FIG. 7 (A–B) shows the multimers extracted from an undyed (A) and dyed (B) cotton towel; in each case the top trace is an extract of the new towel and the bottom trace is an extract after one laundering.
Figure 8:
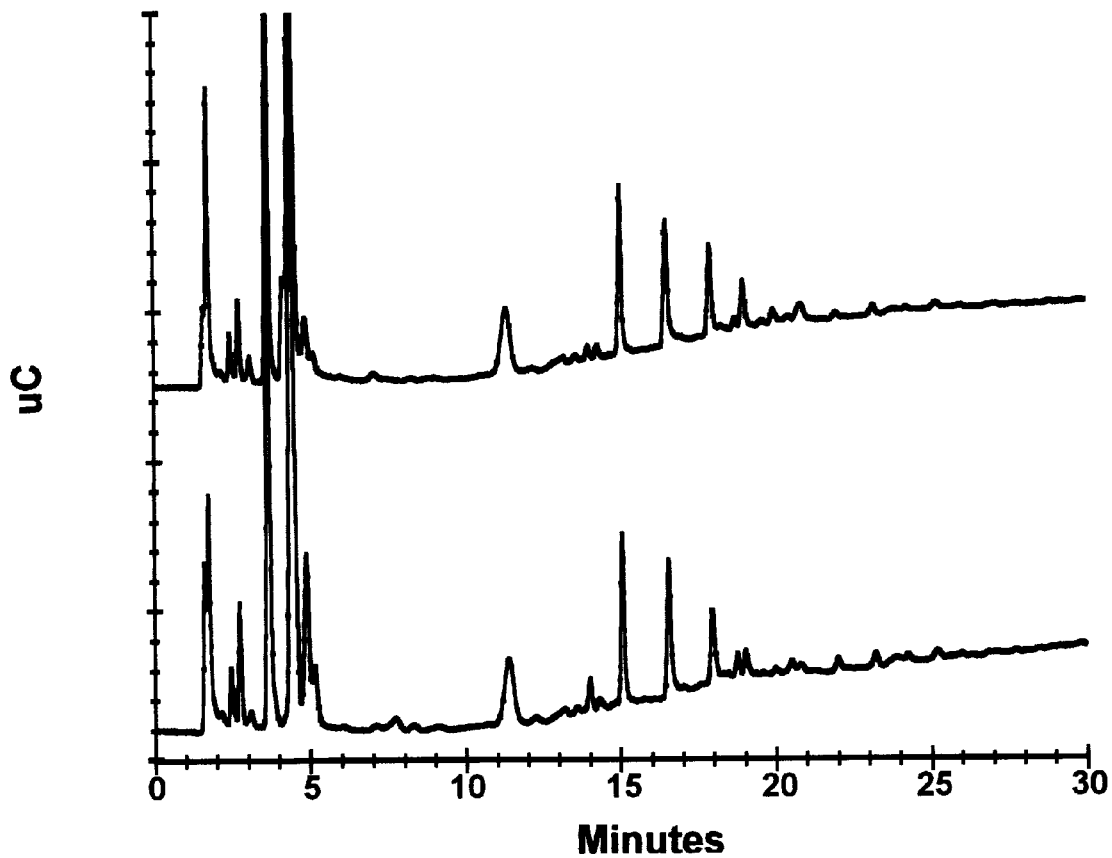
FIG. 8 shows multimers extracted from an old much laundered pillowcase (top) and towel (bottom).

Another surprising finding is that multimers can be extracted from finished cotton fabric as well as from carefully harvested fibers as shown above. FIG. 7 shows multimers extracted by 30 minutes of boiling in 0.1M HCl from an undyed (off white or ivory) cotton towel and from a dyed cotton towel (green). In each case the top trace represents extraction of a new towel and the second (lower) trace shows extraction of a towel that had been laundered one time. Attempts were made to standardize the amount of extracted fabric. Note that the extracted multimers look very similar to those extracted from specially prepared fibers. In this case processing of the fabric has removed all GC-1 and GC-2 compounds so that an aqueous preextraction is unnecessary—there is no danger that the GC compounds might obscure the multimers. The differences in quality and quantity of multimers extracted are due either to differences in the starting cotton or the textile processing between the two different fabrics. Experiments with "permanent press" treated cotton indicates that such treatments significantly alter the quantity and quality of extracted multimers. Another important discovery is that cotton fabrics are capable of yielding multimers even after prolonged wear and washing. FIG. 8 shows multimers extracted from an old towel and an old pillowcase in the inventor's household. These fabrics had been washed dozens of times and still released similar multimers. Clearly, the multimer analysis can be used to measure wear-related changes in cotton fabrics and to analyze various fabric treatments for their long-term effects on fabric wear. Any treatment that inhibits the release of the multimers would be expected to extend the lifetime of the fabric.

Although a dilute acid wash is the preferred way of extracting multimers for analysis, it has been discovered that prolonged (several days) aqueous extraction at elevated temperatures also releases the multimers. Presumably, long exposure to hot water gradually hydrates paracrystalline portions of the cell wall and allows the multimers to be released. This strongly suggests that these materials are gradually released during washing. The loss of these "glue" elements most likely results in a weakening of the fabric. Traditionally it was believed that fabric weakening with age was merely a mechanical effect of wear and washing. These discoveries suggest that washing actually removes a vital binding component from the cotton. Treatments that slow this removal should extend the life of the cotton fabric. Another practical use of multimer extraction is the determination of cotton types used in a given fabric. Extraction of a range of different cotton varieties has shown reproducible multimer differences between some varieties. In particular, certain high-grade cottons are derived from different cotton species. It might be very beneficial to have a simple test to detect adulteration of these premium cottons with less expensive "ordinary" cottons.

Protein Glue and the Multimers

Figure 9:
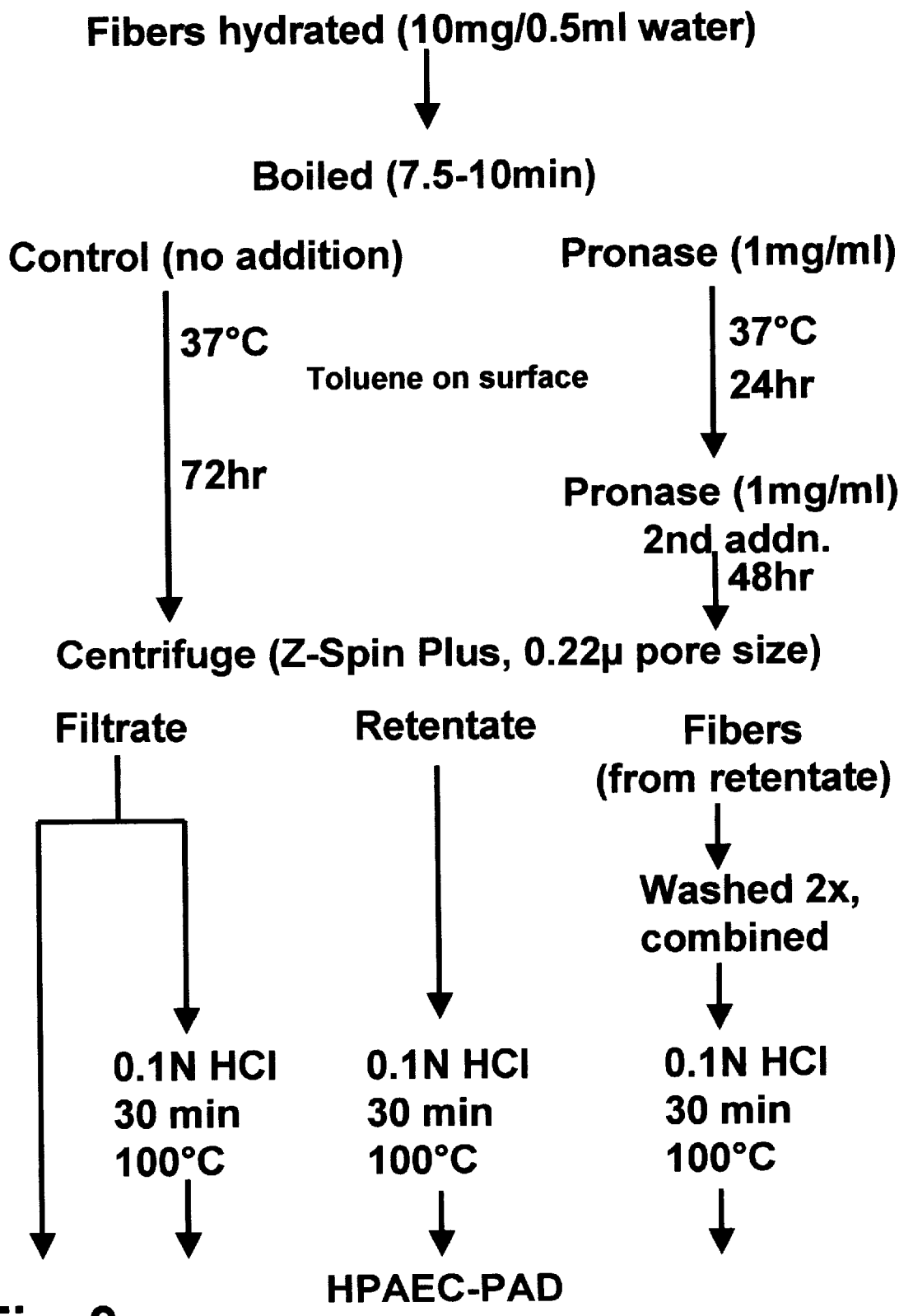
FIG. 9 shows a flow diagram for a proteolytic enzyme experiment with early, midday and late cotton fibers.
Figure 10:
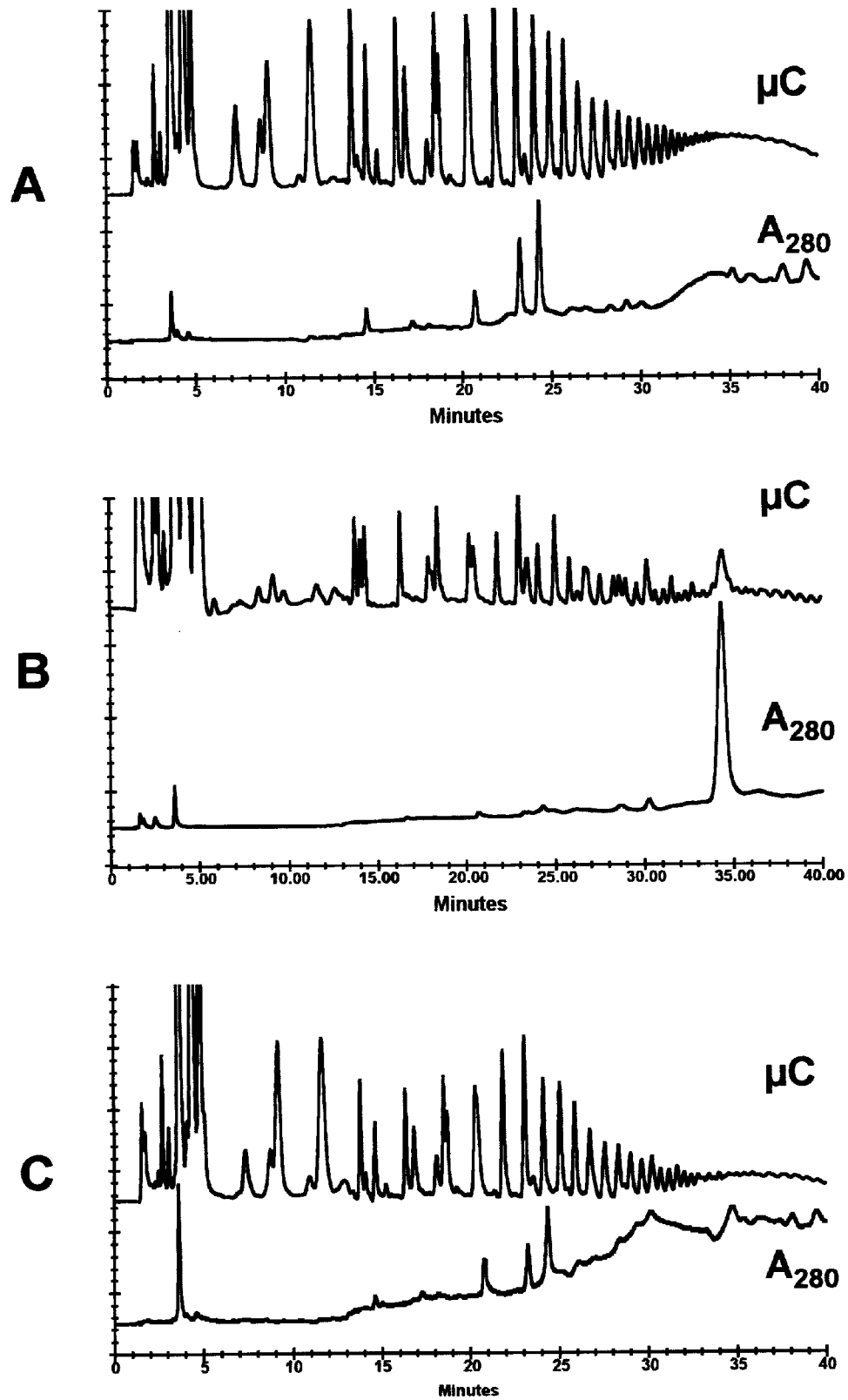
FIG. 10 shows the multimers extracted using the scheme of FIG. 9 for early (A), midday (B) and late C) fibers; besides the carbohydrate multimers, protein is also shown ($A_{280}$).
Figure 11:
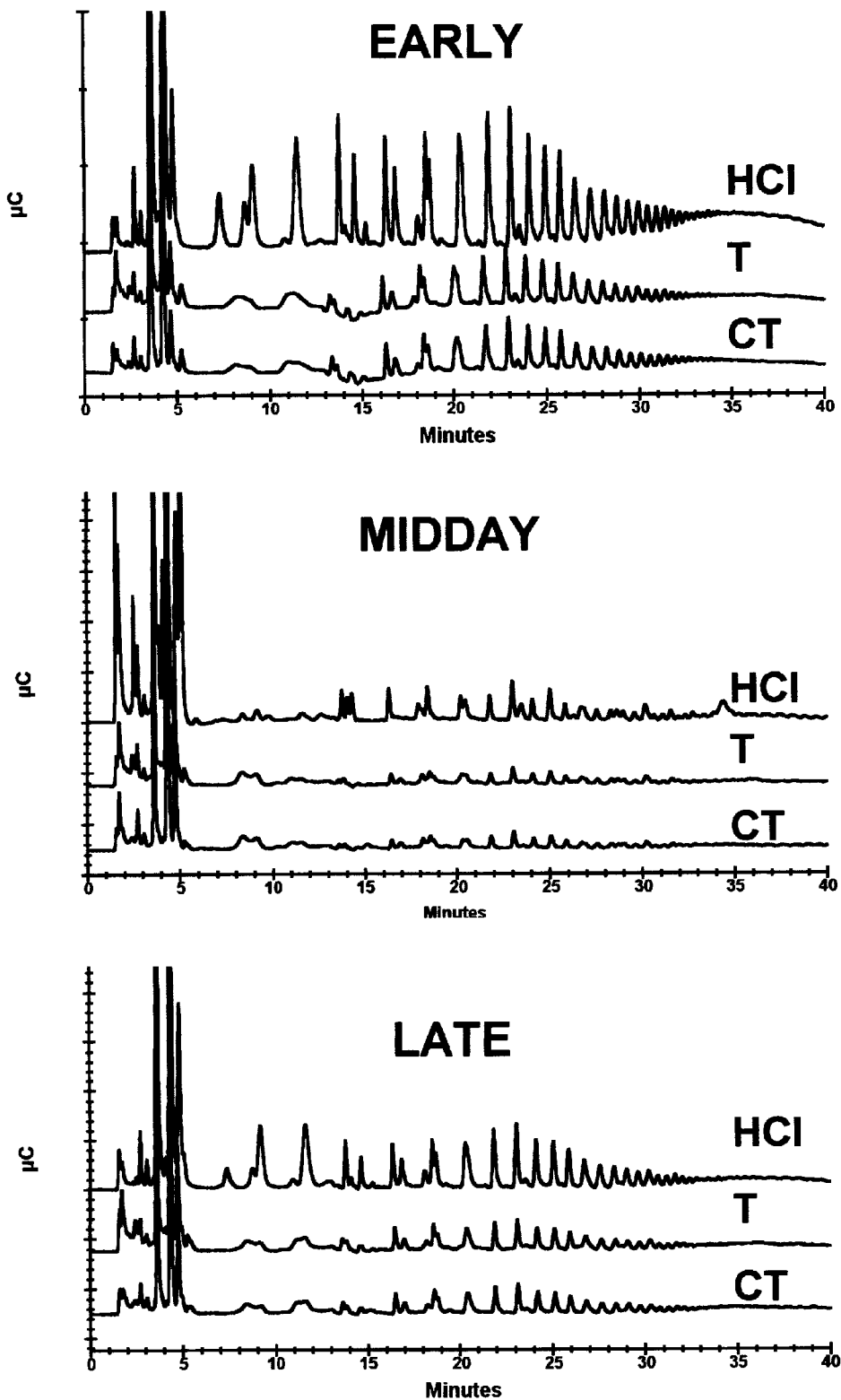
FIG. 11 shows the three multimer extracts of FIG. 10 treated with protease: trypsin (T), chymotrypsin (CT) or 0.1N HCl (HCl).

FIG. 9 shows the flow diagram of an experiment intended to determine what part, if any, protein plays in the cell wall phenomena discussed above. Fibers (25 days post anthesis—DPA) were hydrated and then boiled to denature any enzymes and kill any microorganisms (toluene was also added to additionally insure sterility). The fibers were then incubated at 37° C. for 72 hrs either with or without proteolytic enzyme (pronase 1 mg/ml). At the end of this time the fibers were separated from the supernatant by centrifugation. The supernatant was then passed through a 0.22 μm pore filter to remove any particulate material (this is standard procedure to protect the chromatographic columns). Surprisingly, the supernatants that were not treated with pronase plugged the filters and remained on the filter surface as a gooey material (retentate). The amount of this material depended strongly on the time of day that the source fibers were isolated. As shown in FIG. 10 early (7 am) fibers showed a maximum amount of this material; those from noon fibers showed an intermediate amount; while those from the late (7 pm) fibers showed a minimum amount. It is believed that this gooey retentate represents the "glue" that holds the cellulose in the cell wall. Obviously, rates of cell wall synthesis vary with time of day, and the rate of synthesis might affect the extractability of the glue material. If the filtrate (primarily from the pronase-treated samples) is treated with HCl, a typical multimer pattern is generated. Significantly, if the retentate is treated with HCl or with proteolytic enzyme multimers are generated. This indicates that long-term aqueous extraction removes a cell wall component that includes the multimers. This material is macromolecular and forms a gooey gel. If the material is treated with proteolytic enzyme, the gel is destroyed and the multimers become soluble. The fact that this gel is held together by bonds sensitive to proteolytic enzyme strongly suggests that proteins are important is gluing the cell wall together FIG. 10 shows the multimers produced from the HCl-treated retentate of the early (top graph), midday (middle) and late (bottom) fibers. Each graph shows carbohydrates and protein ($A_{280}$). Note that certain of the multimers are clearly associated with proteins. Further, the precise nature of the proteins changes with time of day. The early and late graphs show a protein triplet peak between 20 and 25 minutes while the midday graph shows a prominent protein peak at about 35 minutes. As shown in FIG. 11, treatment of the samples with either high purity trypsin or high purity chymotrypsin removes the protein components and causes the joint protein/carbohydrate peaks to either disappear or change in shape or position.

Figure 12:
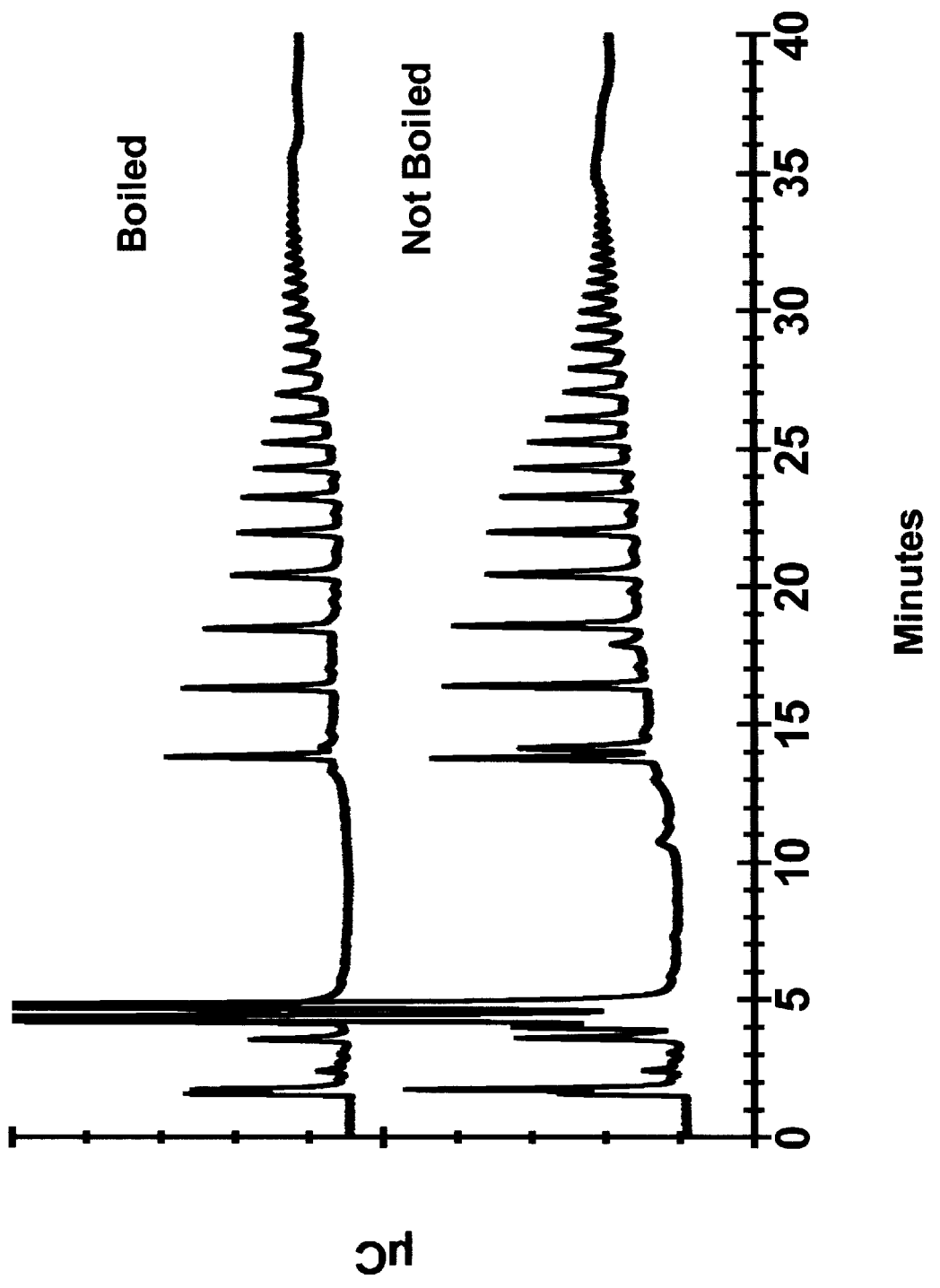
FIG. 12 shows the boiled versus non-boiled extractions performed on fibers harvested in the morning.
Figure 13:
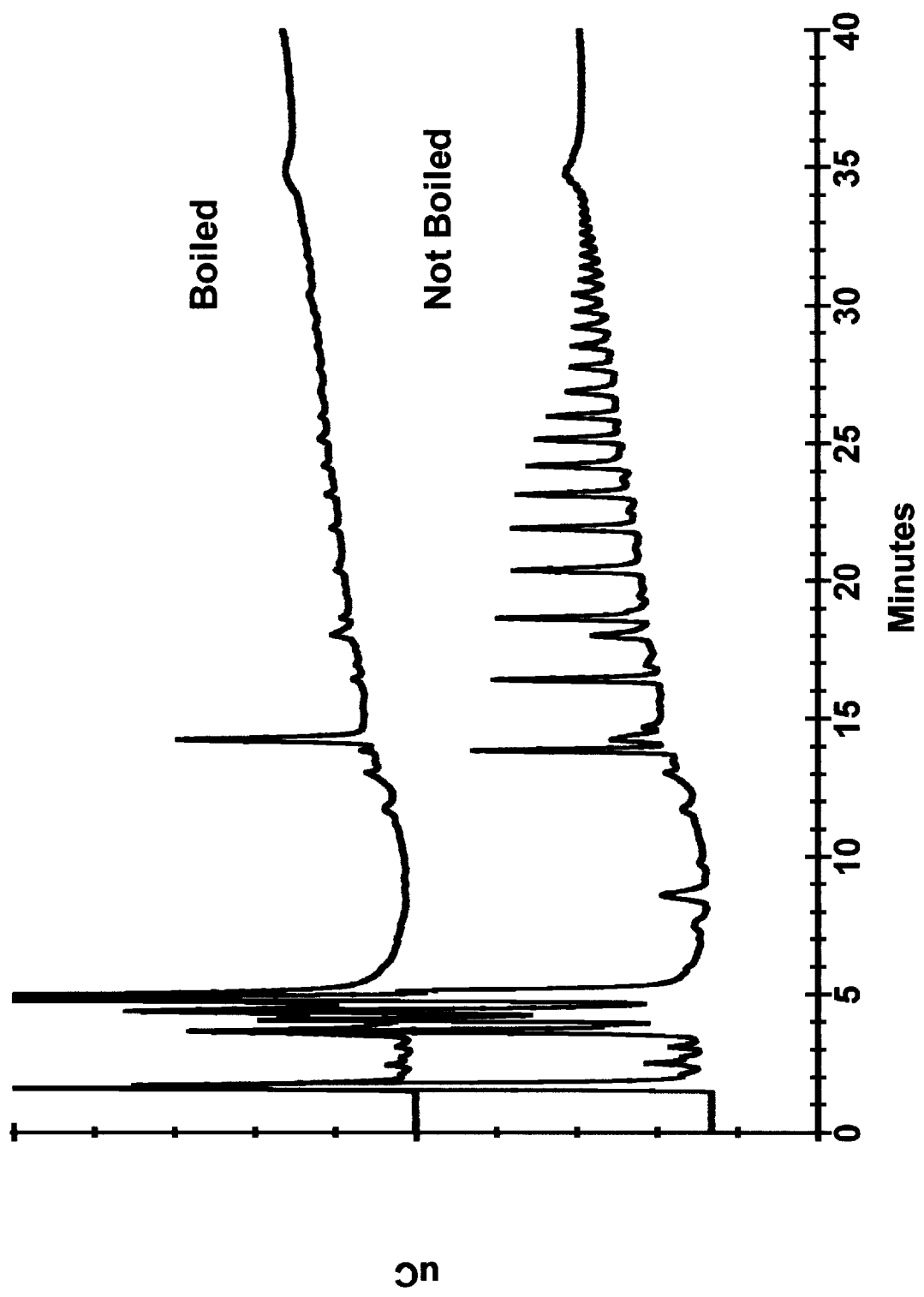
FIG. 13 shows the boiled versus non-boiled extractions as in FIG. 12 performed on fibers harvested at noon.

Boiling the cotton fibers prior to glue extraction resulted in a significant difference in the pattern of multimers that was obtained. With fibers collected in the morning (7 am) boiling resulted in the absence of two or three peaks as shown in FIG. 12. However, with fibers from bolls collected at noon, boiling resulted in the omission of almost all but the first multimer in the series which was relatively more abundant on a per mg fiber basis. This is shown in FIG. 13. Fibers collected in the evening (7 PM) produced a multimer pattern somewhat intermediate but more like the noon fiber pattern. These results are consistent with the fact that the majority of cell wall synthesis occurs at night. The morning fibers represent the material remaining from a night of wall synthesis; noon fibers represent the low point of wall synthesis; and the evening fibers represent the beginning of the wall synthetic process.

Figure 14:
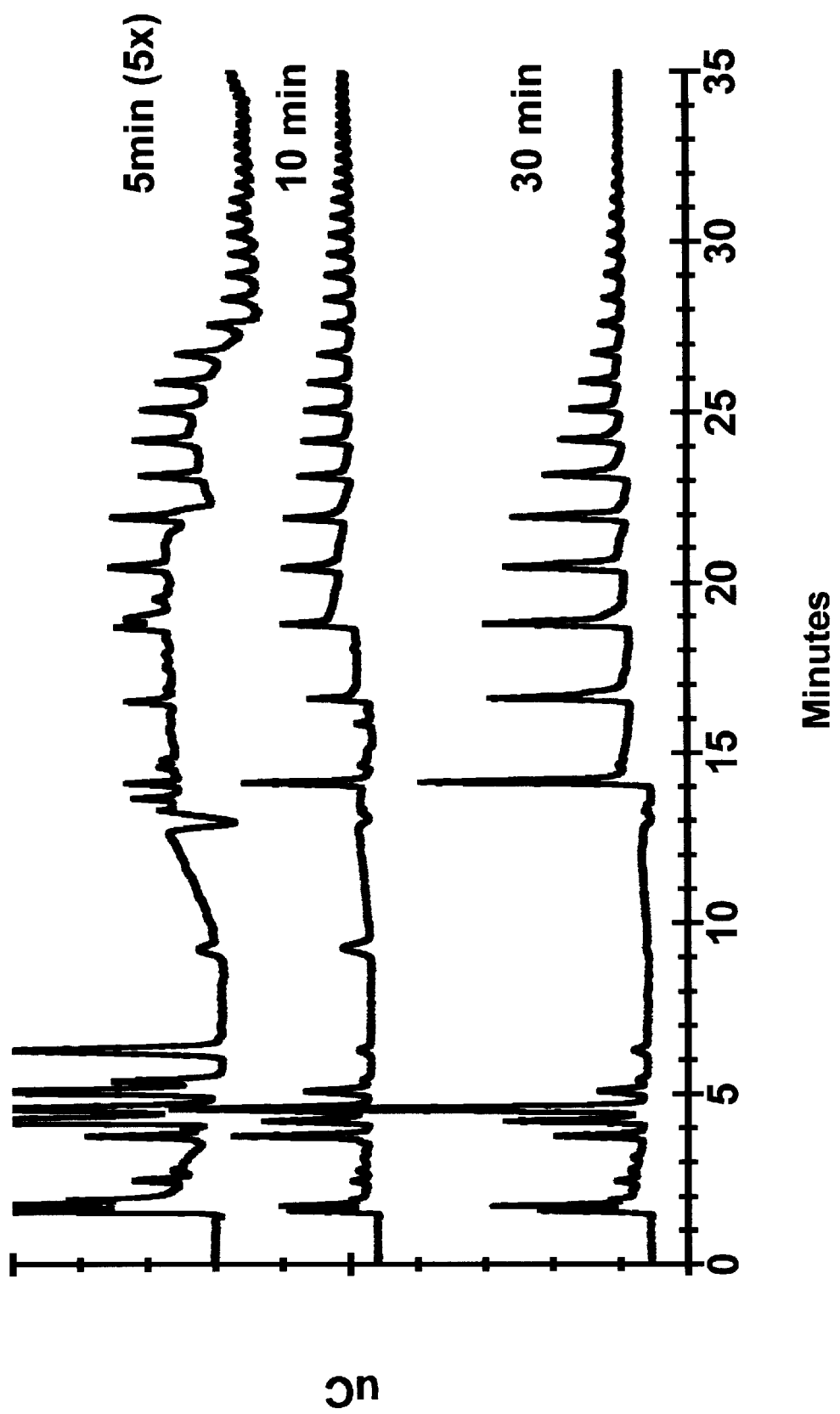
FIG. 14 shows the results of a time course of mild acid hydrolysis of the glue matrix extracted in FIG. 12.
Figure 15:
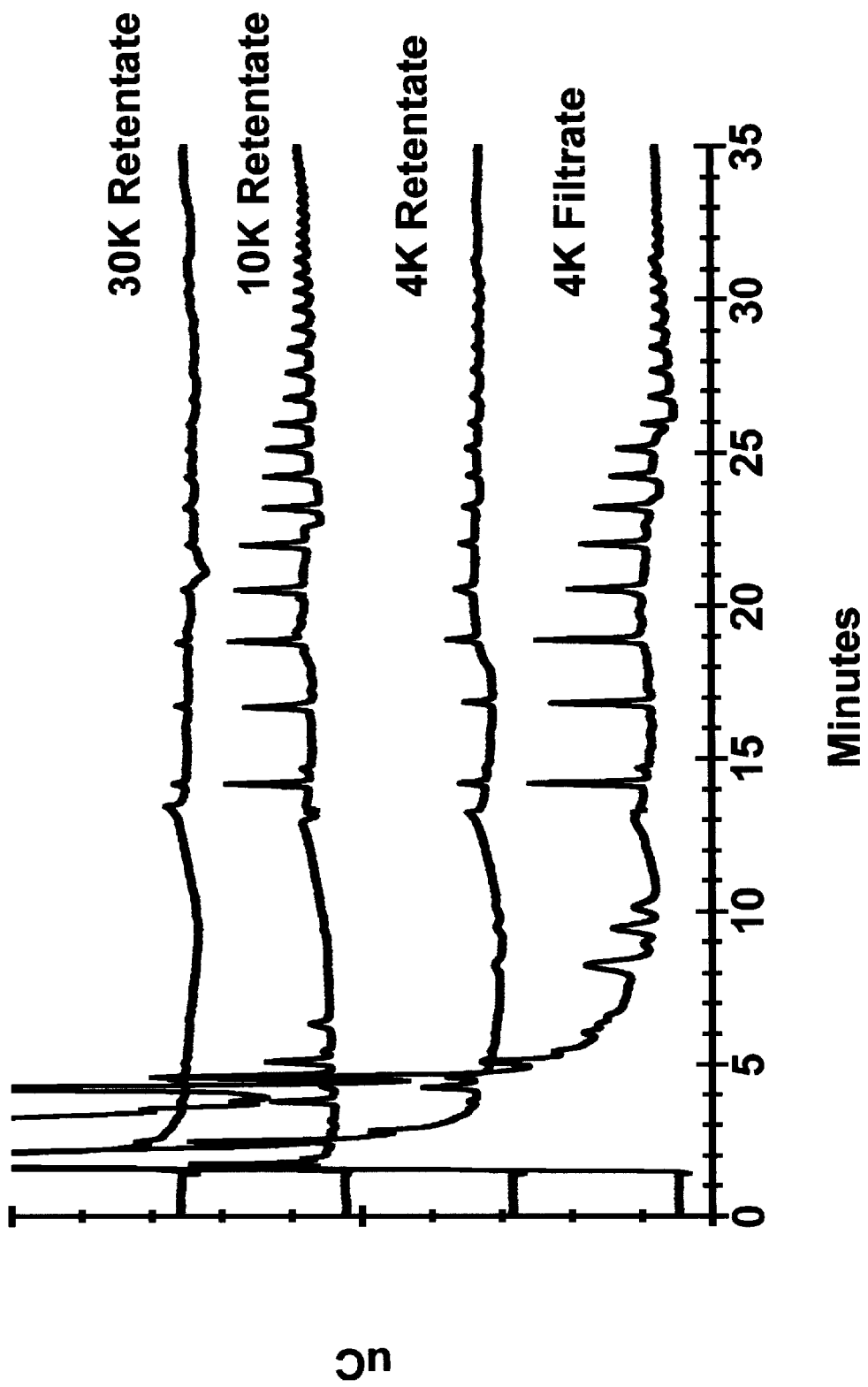
FIG. 15 shows the composition of extracted glue matrix either passed (filtrate) or retained (retentate) by various molecular weight cutoff filters; from top to bottom: 30 kilodalton filter retentate; 10 kilodalton filter retentate; 4 kilodalton filter retentate; and 4 kilodalton filter filtrate.

It is characteristic for the chromatograms of the multimers to show a slight tailing edge on the earlier eluting peaks. This suggests incomplete resolution of peaks. This was investigated by doing a time course of hydrolysis of the glue as shown in FIG. 14. The five-minute time point demonstrates that these early peaks consist of two small peaks which then, with longer hydrolysis times result in one large peak with a tailing edge. This indicates that there are two peaks eluting very near to each other but that one is much more abundant than the other is. This apparent incomplete resolution of peaks was also investigated by subjecting the 30-min hydrolyzate to filtration with molecular weight cut off filters (MWCO). This result is shown in FIG. 15 in which filters of 30,000, 10.000 and 4.000 MW were employed. The major portions of the multimers were obtained in the 10,000 MW retentate or in the 4,000 MW filtrate.

Figure 16:
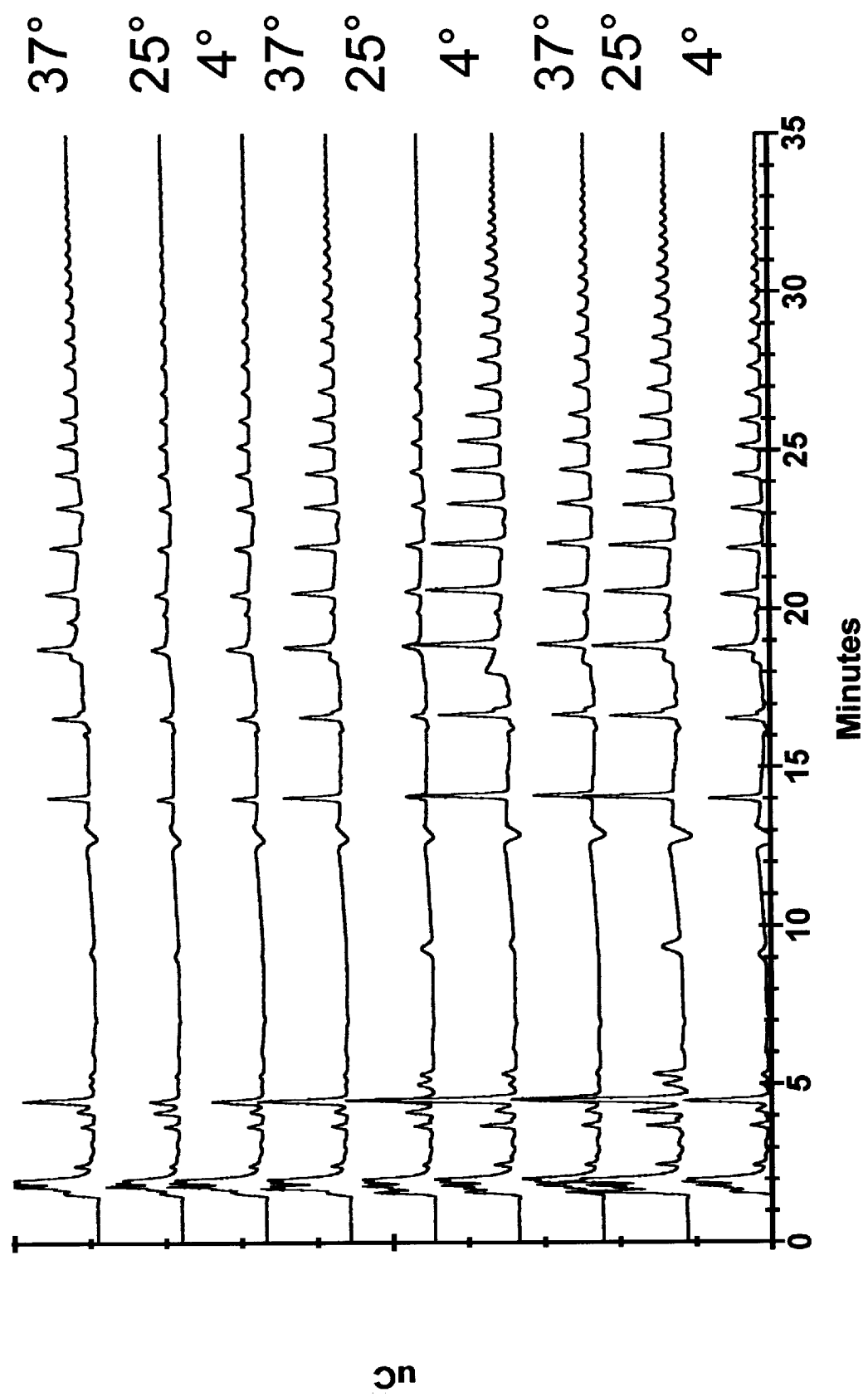
FIG. 16 shows the multimer composition of pellets of extracts from the eighth day of sequential aqueous extraction of 25 day post anthesis fibers collected at three time (morning, noon or evening) and extracted at one of three temperatures: 37° C., 25° C. or 4° C.

Cotton fibers (25 DPA) were extracted with water at three temperatures, 37, 25 and 4° C. for up to 30 days. The extraction tubes were sonicated for 15 min, and filtrates were removed each day and centrifuged to yield a white particulate pellet. It was observed that between 3 and 9 days of extraction the fibers extracted at 4° C. were characterized by one obvious difference. Before sonication the tubes all looked alike but following sonication the 4° tubes became turbid indicative of a very fine particulate suspension. Yet on centrifugation, the pellets obtained from all of the tubes were similar in the quantity of precipitate and in the pattern of multimers obtained (FIG. 16). This result is indicative of a temperature dependent and thus presumably enzymatic process which produces larger particles at the warmer temperatures.

White flakes

Figure 17:
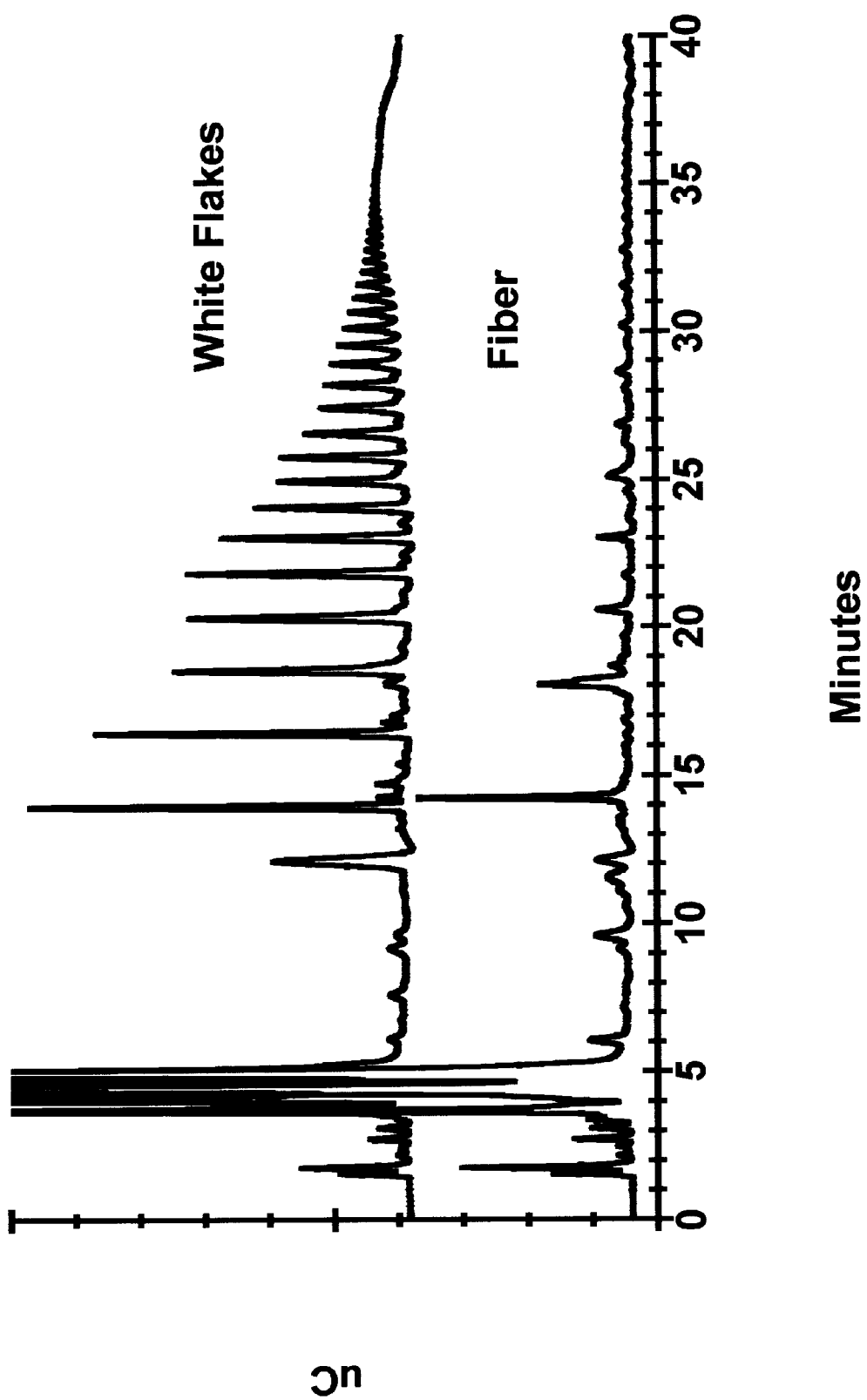
FIG. 17 compares the carbohydrate oligomer composition of fibers with "white flakes" associated with the same fibers.

During the development of the cotton fibers there are some structures present which appear as white flakes in dried material. This material is presumed to result in large part from the drying of the liquid inside the developing carpel; however, the flakes may also be apparent in freshly opened bolls. The flakes are obvious up until at least 39 DPA in many instances, but they disappear in the later stages of development and are gone by the time the bolls open at maturity. Although many investigators have mentioned the white flakes informally, there does not appear to be any investigation of them in the literature. White flakes dissected from the fibers were analyzed for the soluble oligosaccharides. I performed dilute acid extraction to obtain the multimers. On a dry weight basis, the white flakes release at least 5–10 times the quantity of multimers, as do the fibers. This is shown in FIG. 17. Since these white flakes contain multimers that eventually end up in the fibers, the obvious conclusion is that the white flakes contain precursors to the fiber wall. Therefore, all of the developing fiber wall material does not originate within that particular fiber. At this time I do not know if the white flakes originate from a particular population of fibers, other cells in the developing seed coat or other tissues from the inner carpel wall.

Tunicamycin Experiment

Figure 18:
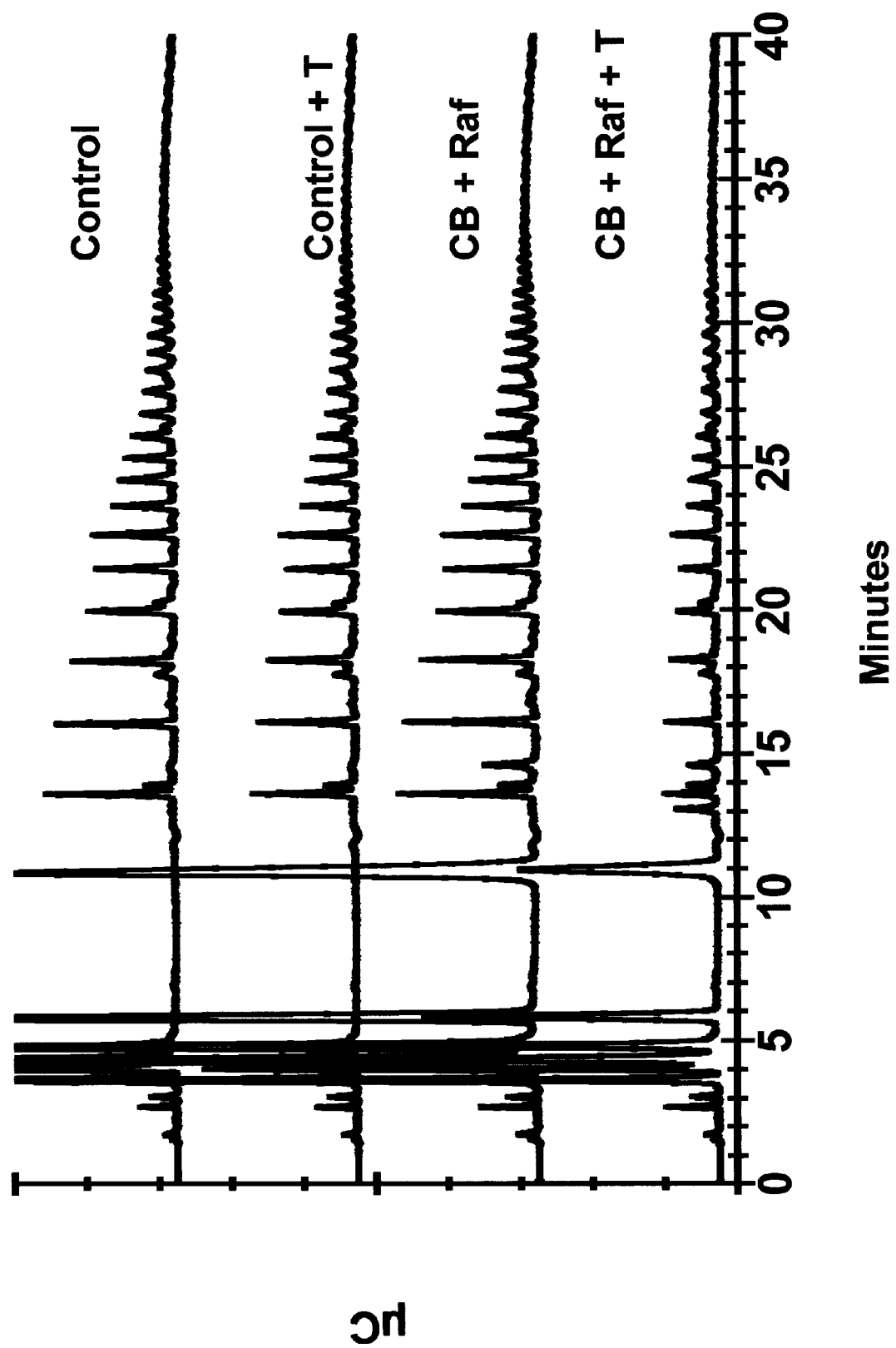
FIG. 18 shows the effects of incubating various substrates (CB=cellobiose, raf=raffinose) with fibers during the extraction process and the effect of added tunicamycin (T) on the process.

The effect of tunicamycin on the multimers obtained from cotton fibers was investigated. Fibers were incubated with water for two days to deplete endogenous substrates and then incubated for another 24 hours with or without tunicamycin (10 µg/ml) both with and without added substrates. Tunicamycin specifically inhibits the formation of the bond between asparagine and N-acetylglucosamine in N-linked glycoproteins. Without added substrates, the tunicamycin had no appreciable effect but with added substrates such as cellobiose and raffinose, the effect was dramatic as the tunicamycin inhibited the quantity and patter of the multimers extracted as shown in FIG. 18. In other experiments, not shown here, the tunicamycin effect was variable if the endogenous substrates were not depleted prior to addition of tunicamycin.

Enzyme Treatments

Figure 19:
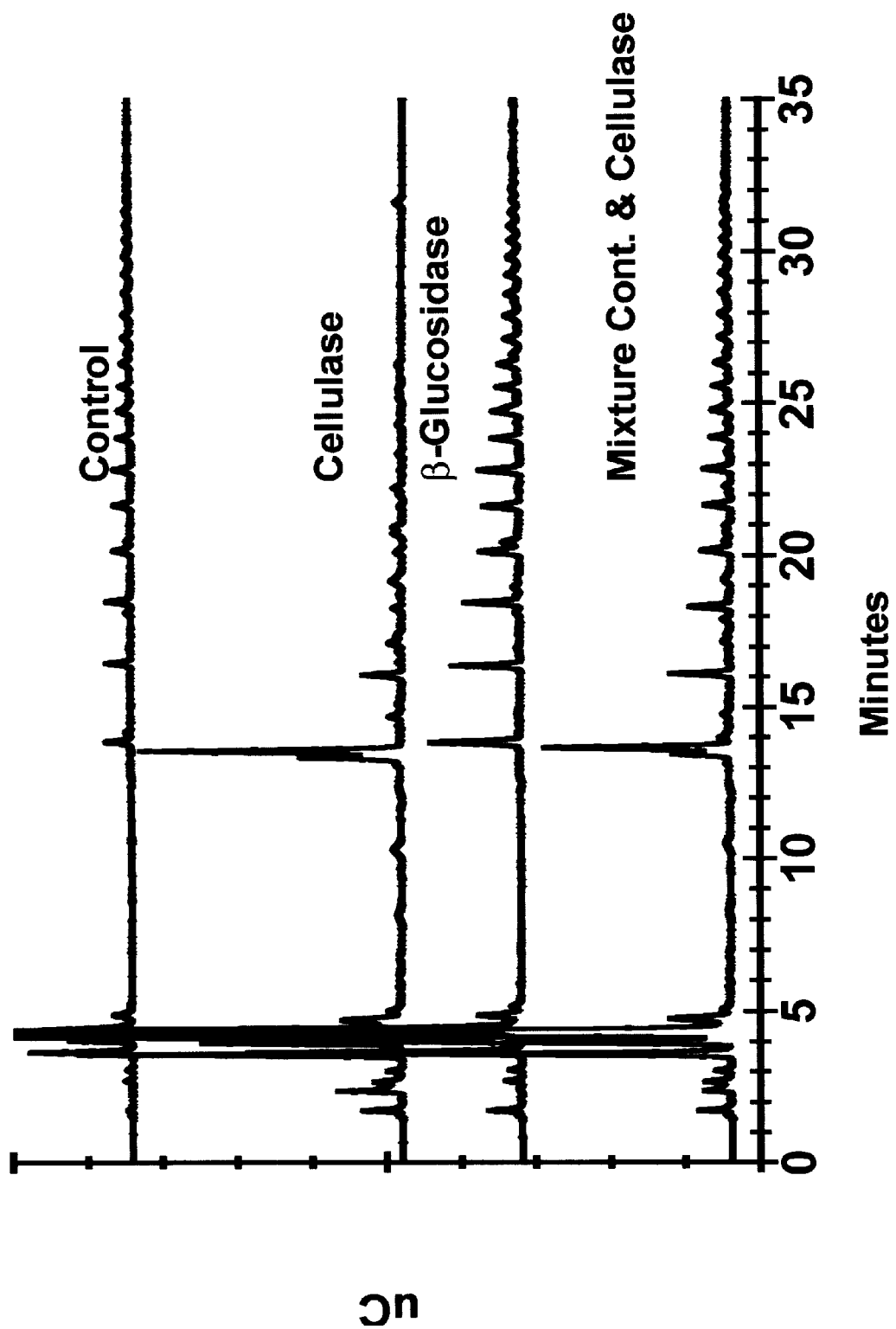
FIG. 19 shows the effect of cellulase or β-glucosidase on isolated multimers; control is the isolated multimers without enzyme treatment.

Extracted multimers were subjected to incubation with a cellulase (*Trichodemna reesei*) or a β-glucosidase (almond emulsin). The effect of the β-glucosidase appeared to be to increase the heights of the multimer peaks significantly and to generate one additional small peak with a retention time slightly greater than 20 min. Presumably this is the result of removing terminal glucose unit(s) that results in a compound with an increased detector response. The cellulase gave a very different result since it resulted in the near elimination of many peaks and great reductions in many peak heights with a great increase in the peak height of the first peak in the series of multimers as shown in FIG. 19. The cellulase result, with the exception of the peak at 11 min (related to cellobiose), was very similar to the profile of the fibers from the stunted plant.

Based on the results of the treatment of the isolated multimers with enzymes, it was decided to attempt to modify the multimers in situ by subjecting the fibers to a sequential enzyme treatment. The goal was to be able to specifically remove the multimers by the chemically gentle and specific enzymatic means. If this could be accomplished then one could make a cogent argument for the multimers as specific components of the fiber cell wall. Fibers (25 DPA) were subjected to a 24 hr incubation with trypsin, chymotrypsin, proteinase K or pepsin followed by a second 24 hr incubation at 37° C. with cellulase or , β-glucosidase. Alternatively, a duplicate set of samples was subjected to the same enzymes but in the reverse order. That is the cellulase or β-glucosidase first and then the protease second. The final fiber/residual material was then subjected to the dilute acid extraction to remove the multimers prior to HPAEC-PAD.

Figure 20:
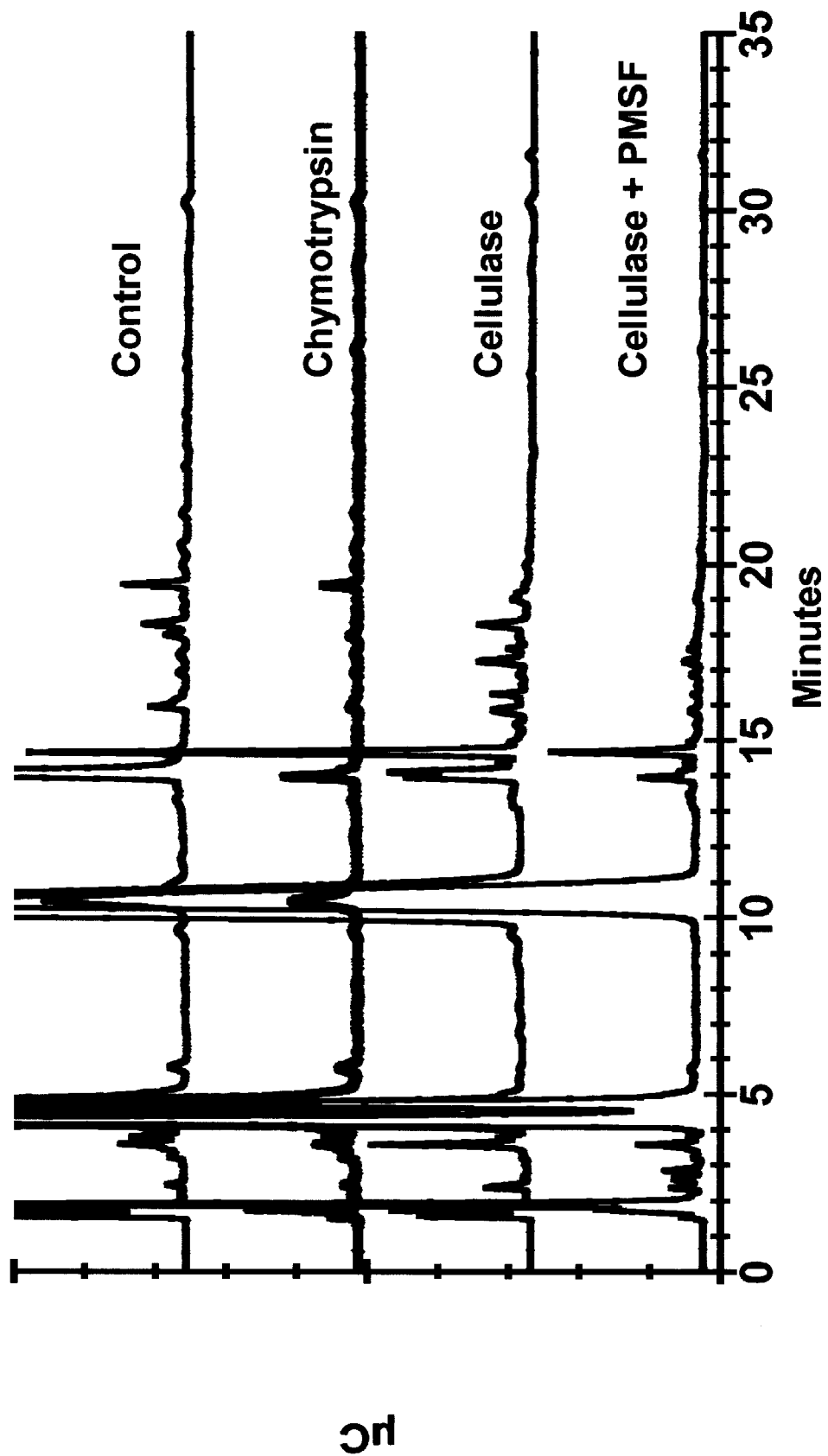
FIG. 20 shows the carbohydrates extracted from the first incubation of fibers treated with protease first (chymotrypsin) or cellulase first; PMSF= phenylmethylsulfonyl fluoride, a serine protease inhibitor.
Figure 21:
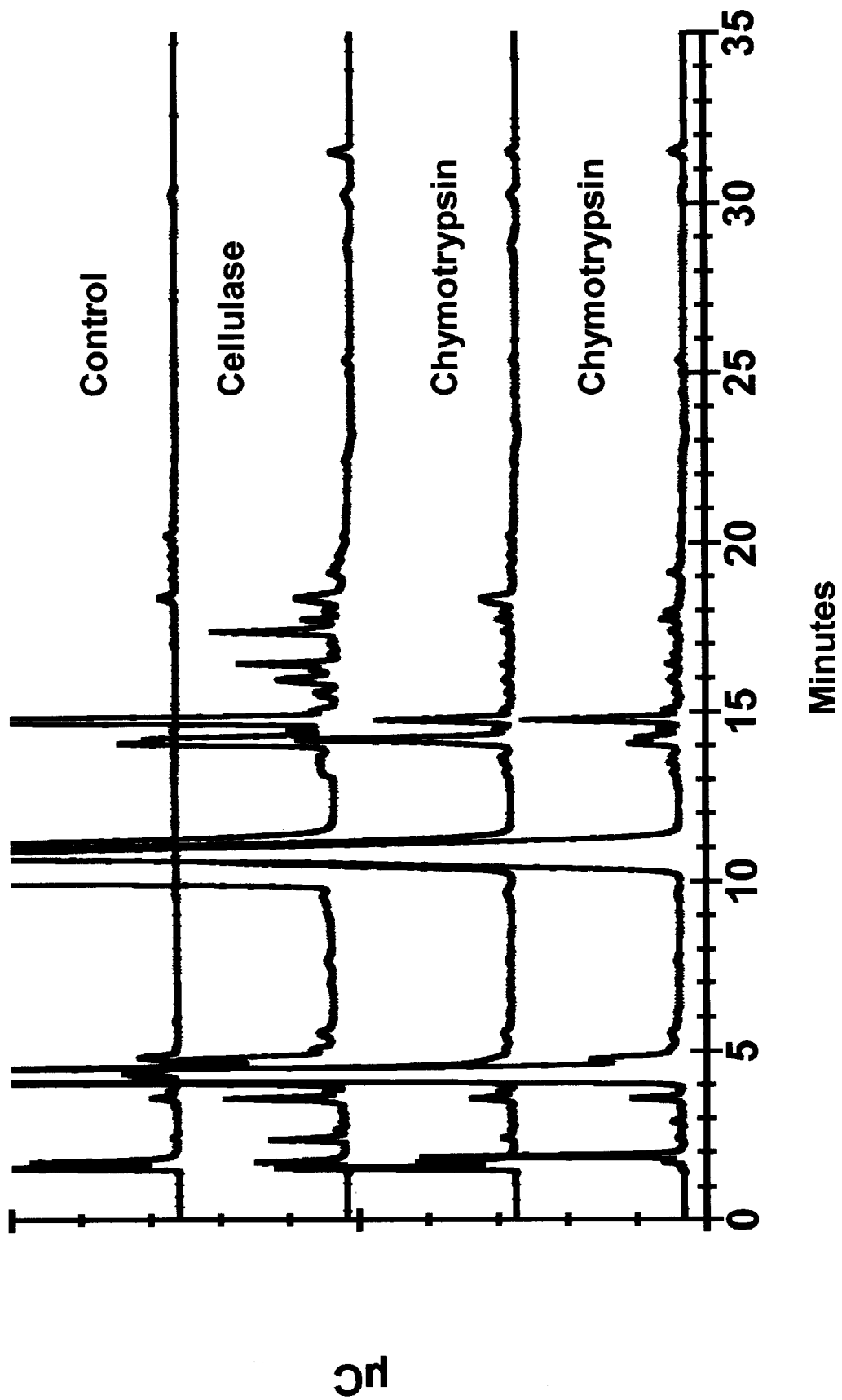
FIG. 21 shows the carbohydrates released from the second incubation of the fibers; the cellulase fibers had a first incubation with chymotrypsin and the chymotrypsin fibers had a first incubation with cellulase.
Figure 22:
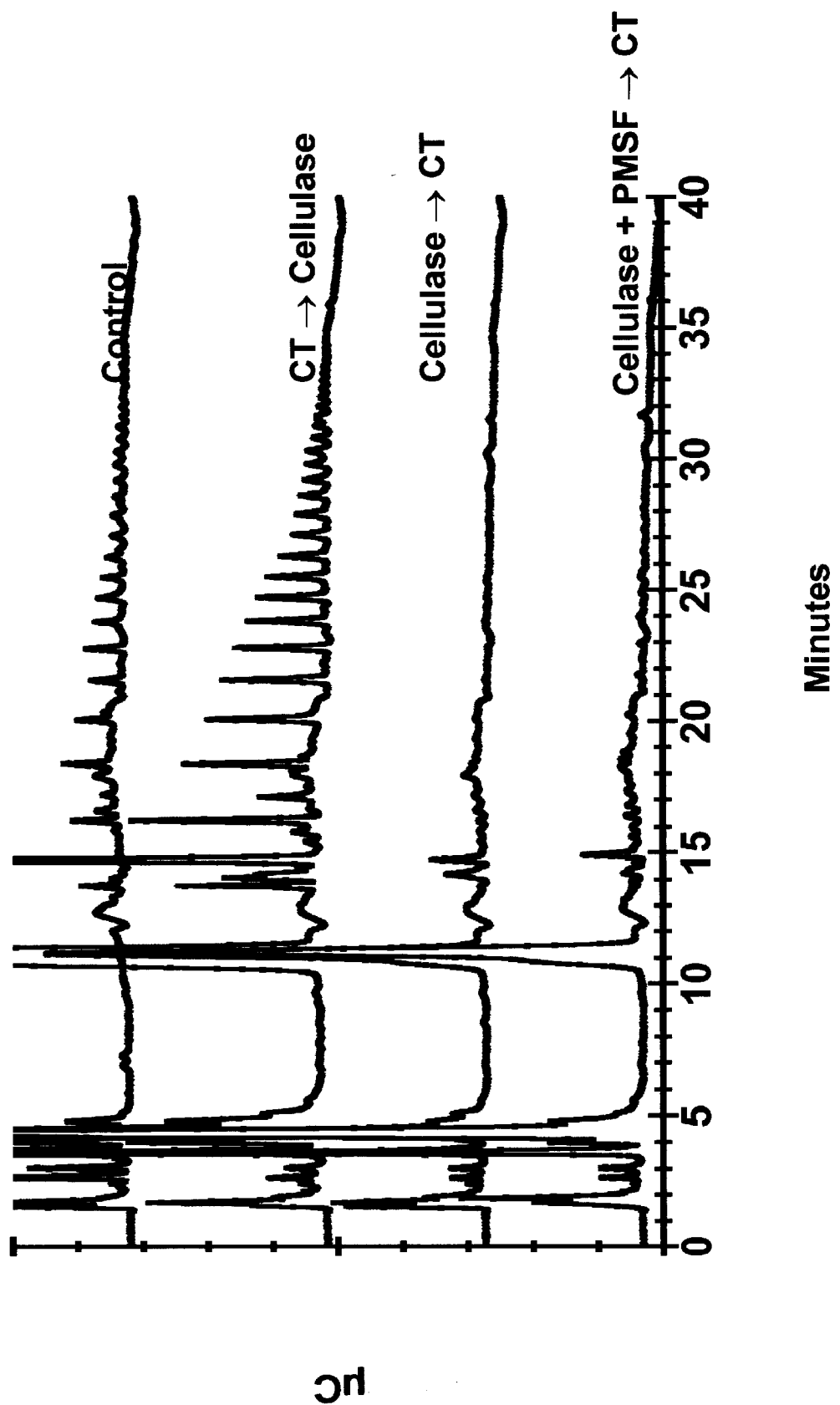
FIG. 22 shows the multimers extracted from the fibers following the two extraction of FIGS. 20 and 21; CT=chymotrypsin, PMSF=phenylmethylsulfonyl fluoride.

As shown in FIGS. 20–22, material was released by both proteases and cellulase or β-glucosidase. The multimers extracted from the final released material (FIG. 22) indicate that multimers could be extracted from the control fibers or fibers subjected to protease first followed by cellulase, but no multimers were obtained from the material subjected to the cellulase first followed by the protease. In that case chymotrypsin was the most effective protease just as it was for degradation of the glue. However, the most striking observation was that the fibers treated with cellulase followed by protease lost their structural integrity and simply fell apart or were sucked up into the Pasteur pipette when the extract was removed.

When mature fibers from opened bolls were subjected to the same cellulase followed by protease procedure, very little happened so the procedure was repeated a second time. At the end of the second cycle, the fibers completely lost their structural integrity and only a precipitate of very small particles remained. These particles were then washed, subjected to digestion either in dilute HCl, in 2N trifluoroacetic acid or in 6N HCl. Actual digestion occurred only in 6 N HCl, and the resulting monosaccharides obtained appear to be in excess of 99% glucose. This indicates that sequential treatment with cellulase followed by protease is an excellent method for producing cellulose of extremely high purity. This result is striking since it provides evidence for significant modification of the fiber walls associated with boll opening and maturity. This means that even though the cellulosic fiber wall is deposited in daily growth layers, there is obviously a very significant post-depositional modification process that drastically alters the fiber wall properties.

Figure 31:
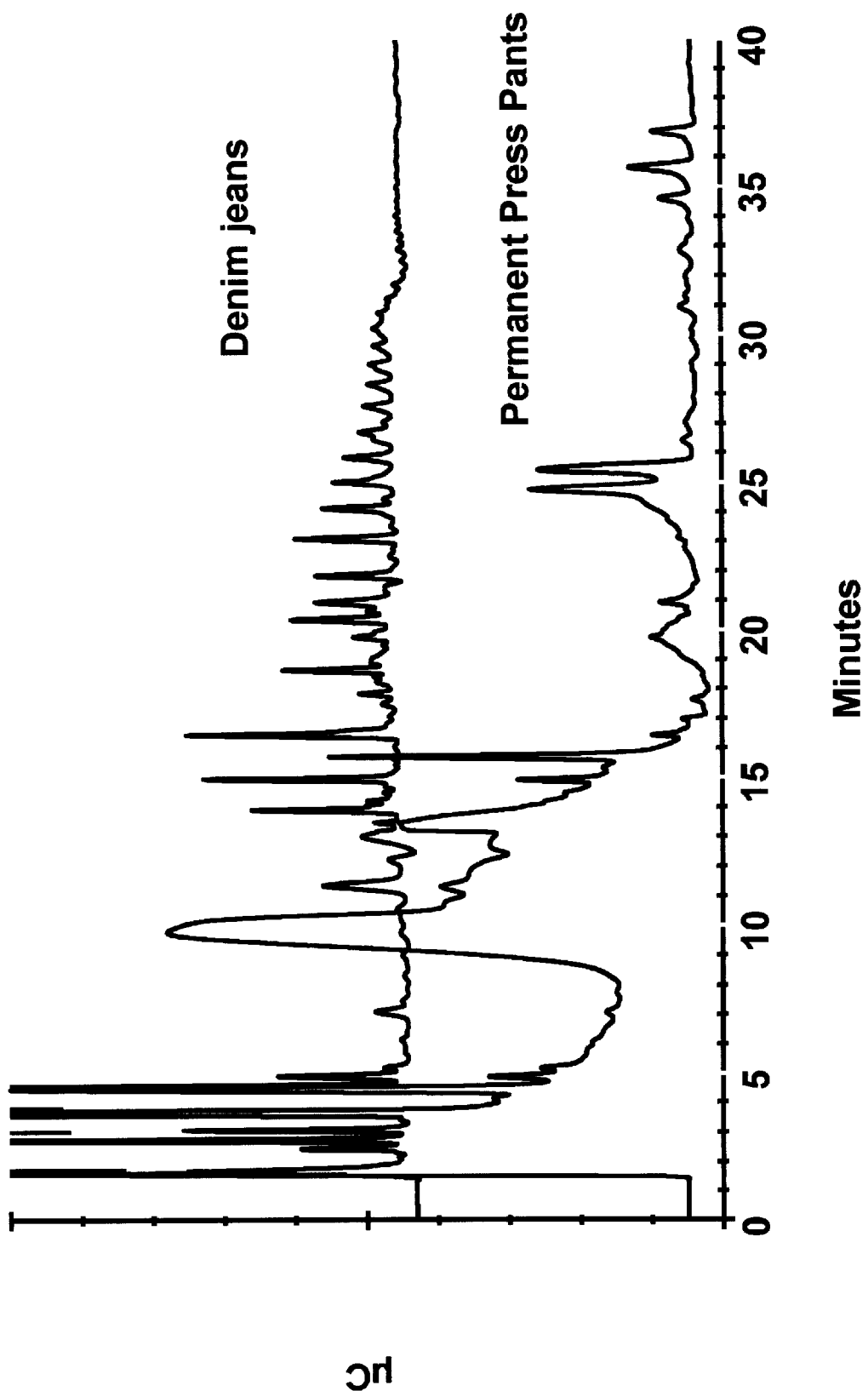
FIG. 31 shows multimers extracted from old (heavily laundered) denim jeans (a) as opposed to permanent press pants (b) in which the multimers appear to have been cross-linked.
Figure 32:
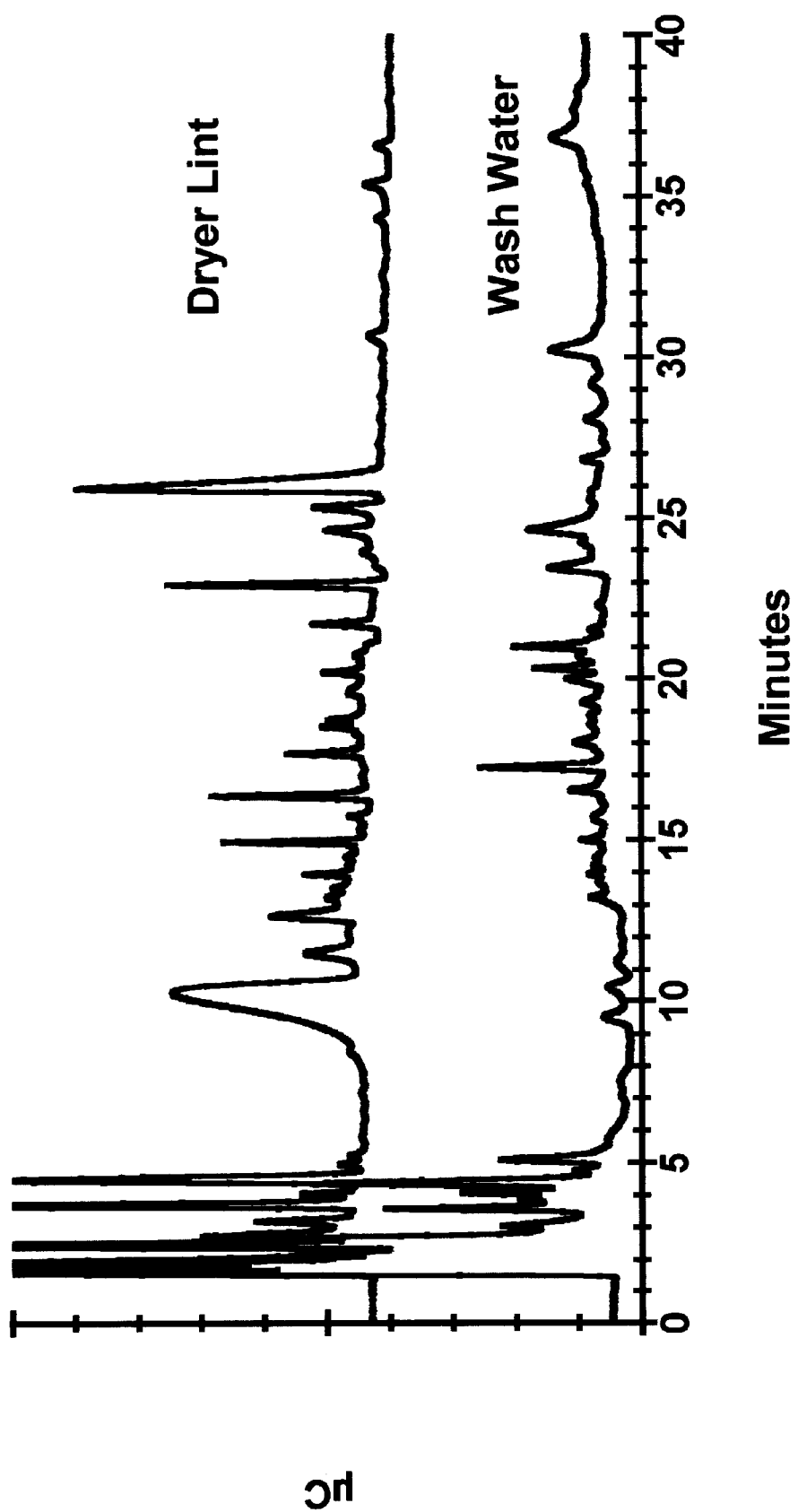
FIG. 32 shows multimers extracted from dryer lint (a) (similar to whole fabric) versus multimers found in wash water (b) released from laundering cotton fabric.
Figure 33:
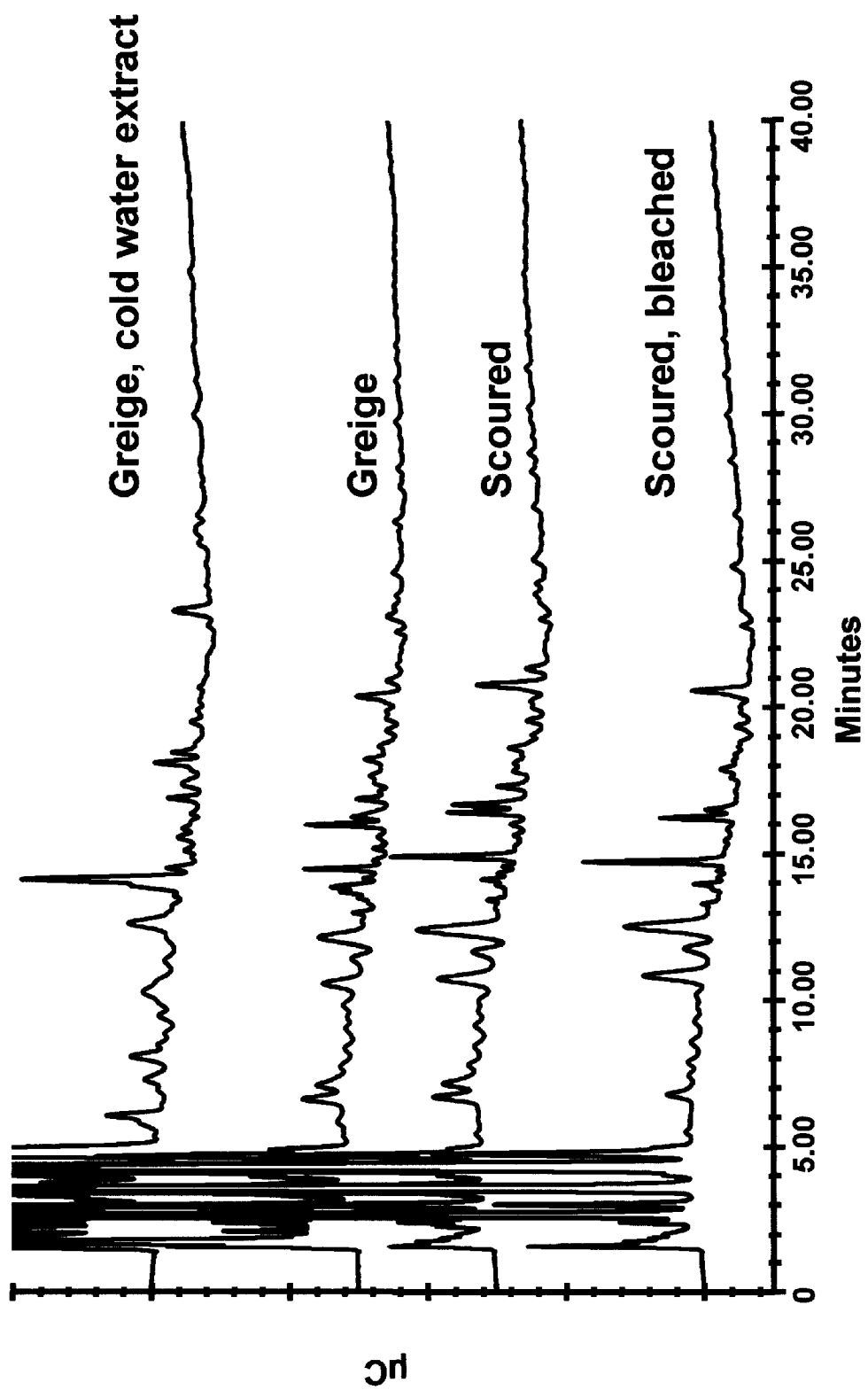
FIG. 33 shows multimers extracted from cotton fabrics at various stages of processing: a) Greige stage with cold water extraction; b) Greige stage; c) scoured fabric; and d) scoured fabric that has been bleached.
Figure 34:
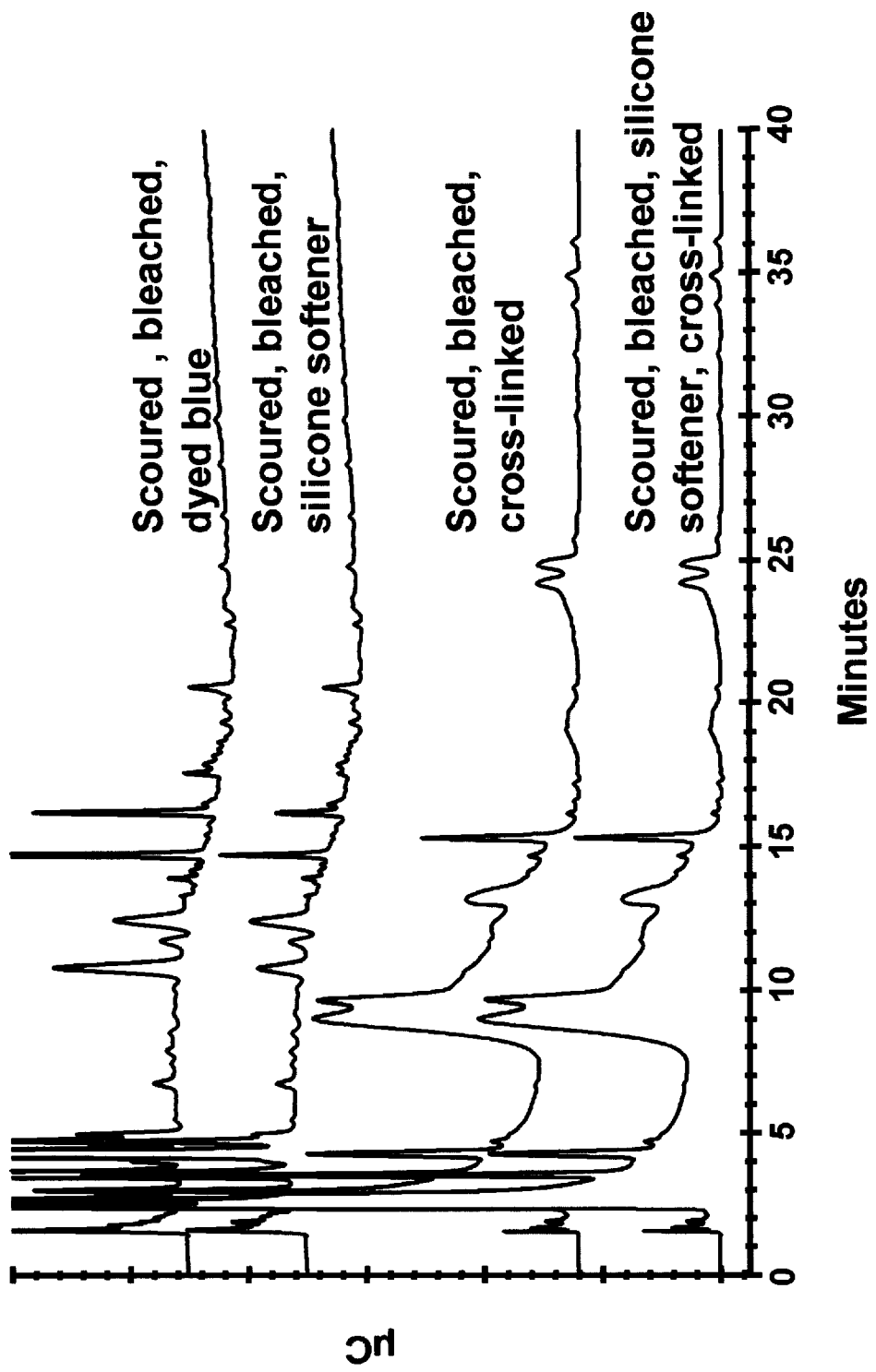
FIG. 34 shows multimers extracted from cotton fabrics at various stages of processing: a) scoured, bleached and blue dyed fabric; b) scoured, bleached with a silicone fabric softener; c) scoured, bleached and cross-linked; and d) scoured, bleached, and cross-linked with a silicone fabric softener.

Samples of cotton fabric from various stages of the textile production process were subjected to this method of analysis FIG. 33 shows examples of cotton fabric from the Greige mill stage (using both cold water extraction method described in the original parent application as well as the 0.1N HCl extraction method described in the more recent parent applications), which is prior to any wet processing steps. FIG. 34 shows multimers from fabric which has been scoured and then subjected to additional treatments: scoured, bleached and dyed blue (FIG. 34*a*), scoured bleached and treated with a silicone fabric softener (FIG. 34*b*), scoured, bleached and cross-linked (FIG. 34*c*), or scoured, bleached, treated with silicone softener and cross-linked (FIG. 34*d*). It is evident that there are alterations in the multimer peaks obtained from each step of the processing FIG. 31 show multimers released from old denim pants (FIG. 31*a*) as well as permanent press pants (e.g., cross-linked fabric)(FIG. 3*b*). FIG. 32 shows the presence of these multimers in clothes dryer lint and laundry wash water.

Protein Glue and Cross-linking

The probability that cellulose microfibrils of the plant cell wall are embedded in a matrix that "glues" them together has been proposed by a number of investigators over the years. The nature of such a glue matrix has been the subject of considerable discussion but there has been no characterization of such a matrix material. The presence of cell wall subunits, in cotton fibers, was proposed by W. Lawrence Balls (Balls, W. Lawrence, 1928, Studies of Quality in Cotton, Macmillan & Co., London.) The present work (see above) on the cell wall "glue" matrix is an extension of work in my laboratory to characterize soluble oligosaccharides and the sucrosyl oligosaccharides in particular which appear to be involved in developmental changes of the cotton fiber.

Mature fibers from opened bolls were extracted with cold water and the extract was removed. Cross-linking was then accomplished using water-soluble carbodiimide in unbuffered water at a pH of between 5.0 and 5.2. Two concentrations of water-soluble carbodiimide were used, 125 mM and 250 mM. The cross-inking reaction was carried out for 2 hr at room temperature followed by overnight at 4° C. The reaction mixture was washed from the fibers and the enzymatic digestion then ensued. The fibers were incubated with cellulase (*T. reesei*)(1 mg/mil) for 24 hrs followed by chymotrypsin (CT) (1 mg/ml) and the incubation sequence was then repeated. The results are shown in FIGS. 23–26. In all cases, samples number 1 are the controls; number 2 are the fibers from the 125 mM carbodiinide reaction and number 3 are the fibers from 250 mM carbodimide reaction. Under the reaction conditions the carbodiimide would be expected to promote amide bond formation between amino acids while having negligible effect on ester bond formation between carbohydrates.

As explained above, a series of multimers (oligomers) can be extracted from developing cotton fibers by both chemical and enzymatic methods. These multimers have retention times of 14 minutes and greater under the analysis conditions employed. The regular spacing of the peaks is indicative of a series of oligosaccharides varying by a unit monomer in size. These results indicate that the multimers are heteropolymers with a repeating glucan unit extending from a core peptidoglycan structure. Above it was shown that the structural integrity of 25 DPA cotton fibers can be degraded by a sequential enzymatic treatment with a cellulase followed by a protease whereas the reverse extraction sequence does not result in complete degradation. When fibers from bolls that have opened are subjected to the same extraction sequence, they do not lose their integrity unless the process is repeated a second time. Following the second protease treatment, the fibers disintegrate into a white particulate precipitate.

Figure 23:
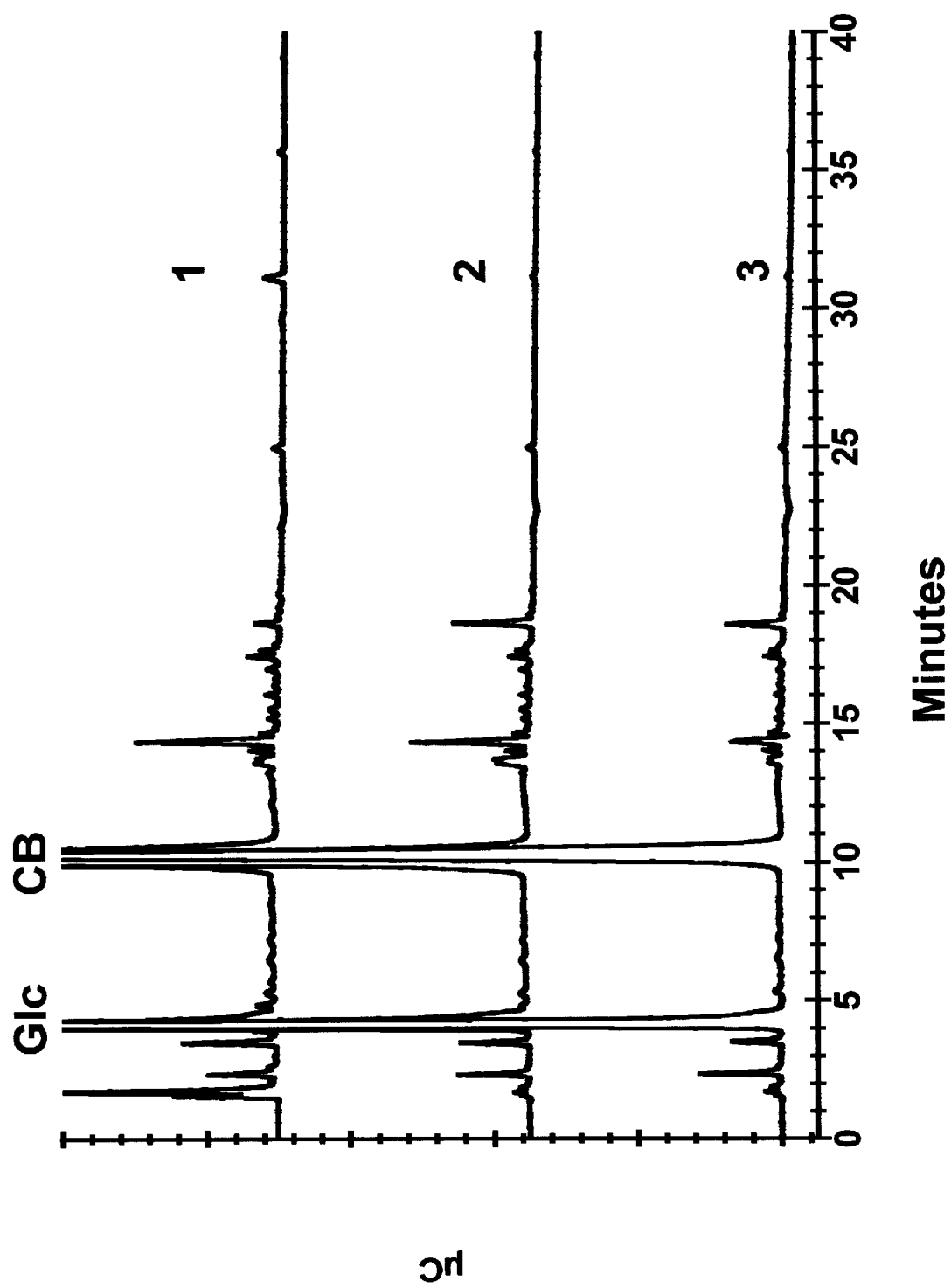
FIG. 23 shows carbohydrates released by cellulase without cross-linking (1) or following cross-linking with either 125 mM (2) or 250 mM (3) carbodiinide.

Quantitatively the constituents released by enzymatic treatments consist mainly of glucose (Glc) and cellobiose (CB). Carbohydrates released by the first cellulase treatment are shown in FIG. 23 which demonstrates that carbodiimide at either concentration dramatically reduced the amount of glucose or cellobiose released by the cellulase treatment. The peak at 3.5 min retention time is arabinose. Many more of the peaks in the 14–20 min range are released by the cellulase from the control fibers than from the treated fibers. The major peak with a retention time of approximately 14.5 min released from the control fibers has a distinctly shorter retention time than the major peak at about 14.65 min released from the treated fibers. This is a significant difference and it only is demonstrable in the first cellulase extract.

Figure 24:
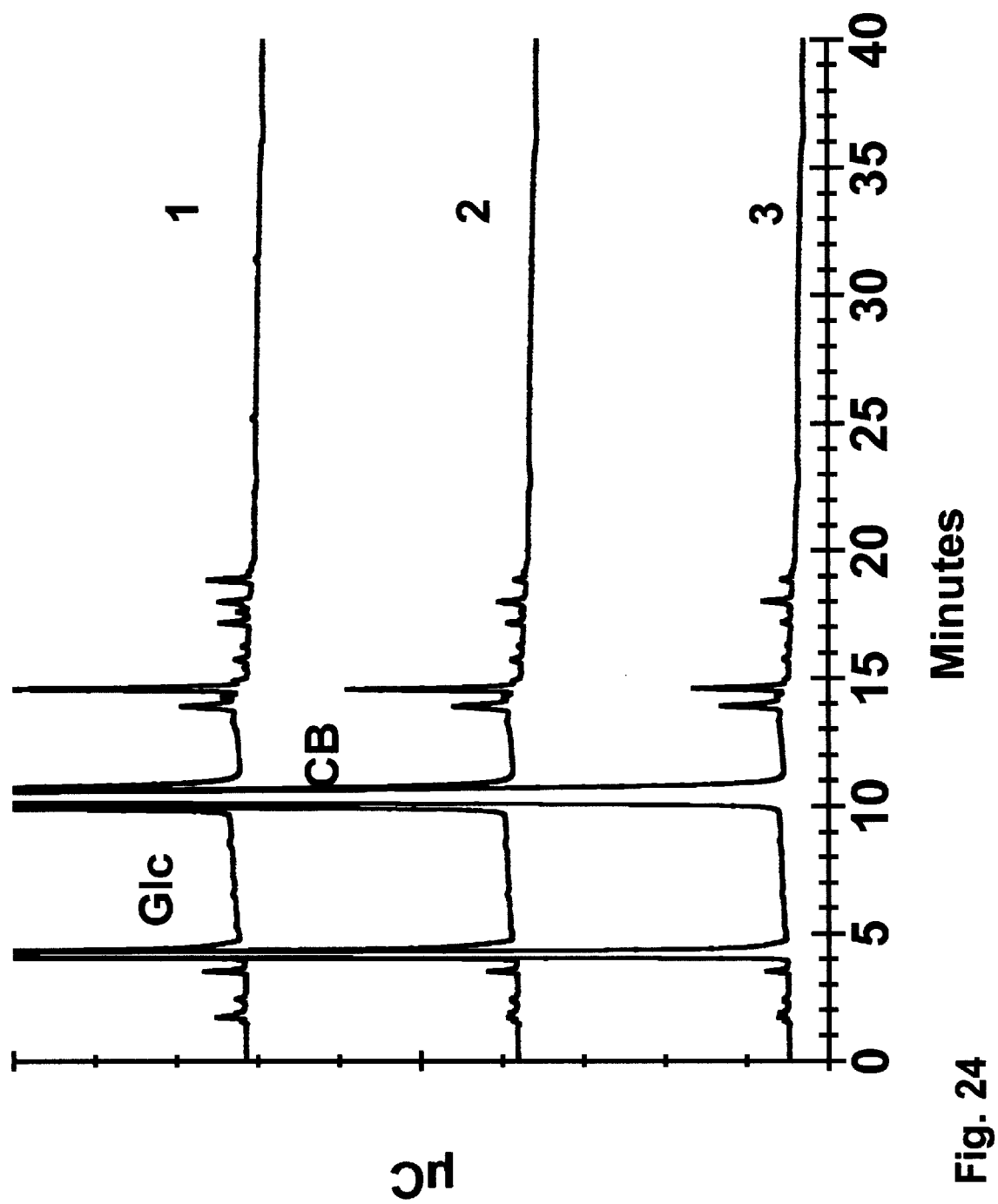
FIG. 24 shows carbohydrates released by chymotrypsin after the cellulase alone treatment (1) or after cross-linking with either 125 mM (2) or 250 mM carbodiimide (3) and a cellulase treatment.
Figure 25:
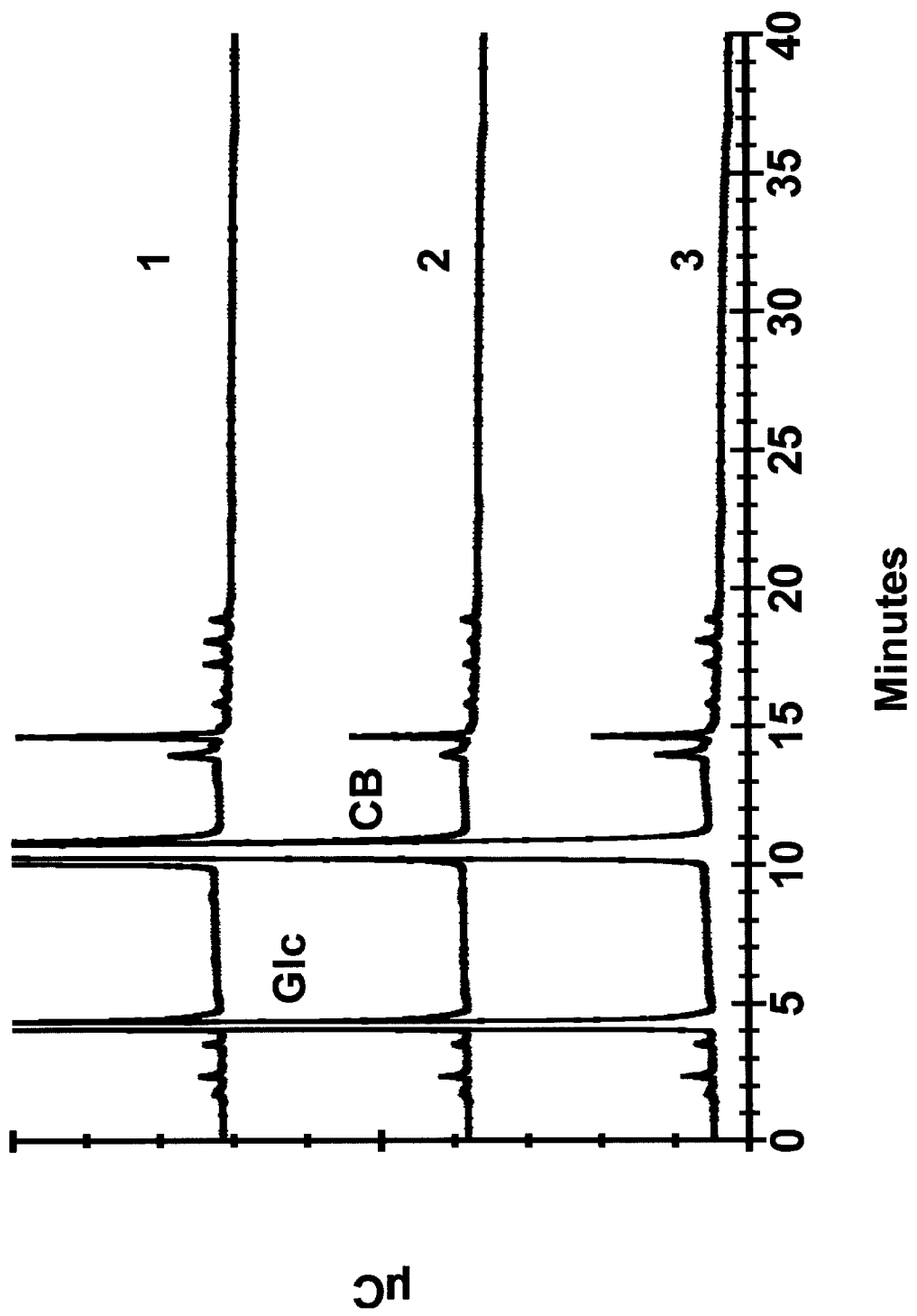
FIG. 25 shows carbohydrates released by a second cellulase treatment (following the first cellulase and chymotrypsin treatments) alone (1) or following cross-linking with either 125 mM (2) or 250 mM (3) carbodiinmide.
Figure 26:
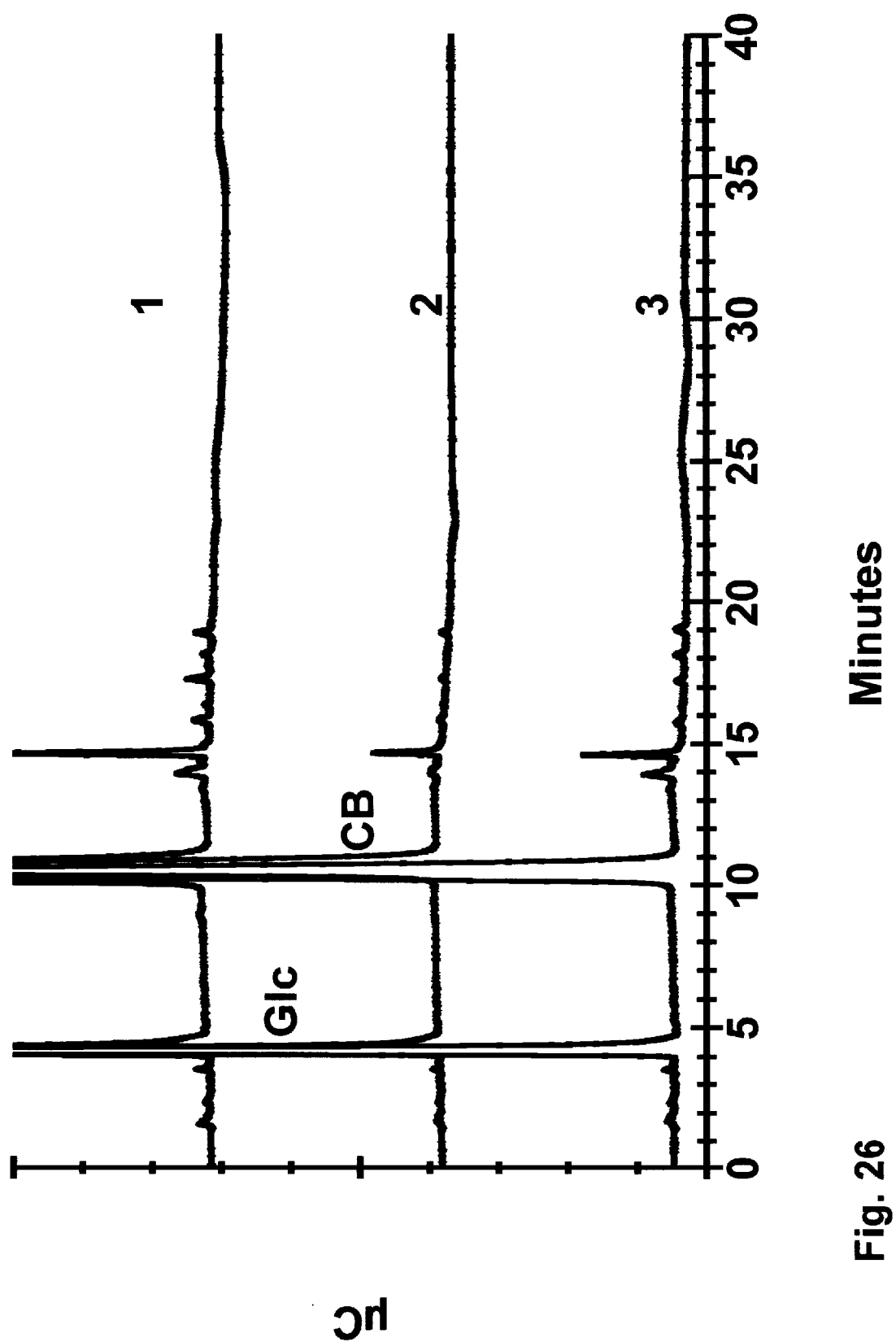
FIG. 26 shows carbohydrates released by a second chymotrypsin treatment (following the first cellulase, chymotrypsin and second cellulase treatments) alone (1) or following cross-linking with either 125 mM (2) or 250 mM (3) carbodiimide.

The carbohydrates released by the first chymotrypsin treatment are shown in FIG. 24. More peaks in the 14–20 min range are released from the control fibers than the treated fibers in addition to the large amounts of glucose and cellobiose released from both treated and controls fibers. This pattern is consistent for the carbohydrates released by the "second" cellulase treatment (actually a cellulase treatment following a chymotrypsin treatment) (FIG. 25) and "second" chymotrypsin treatment (actually a chymotrypsin treatment following a cellulase treatment)(FIG. 26).

Figure 27:
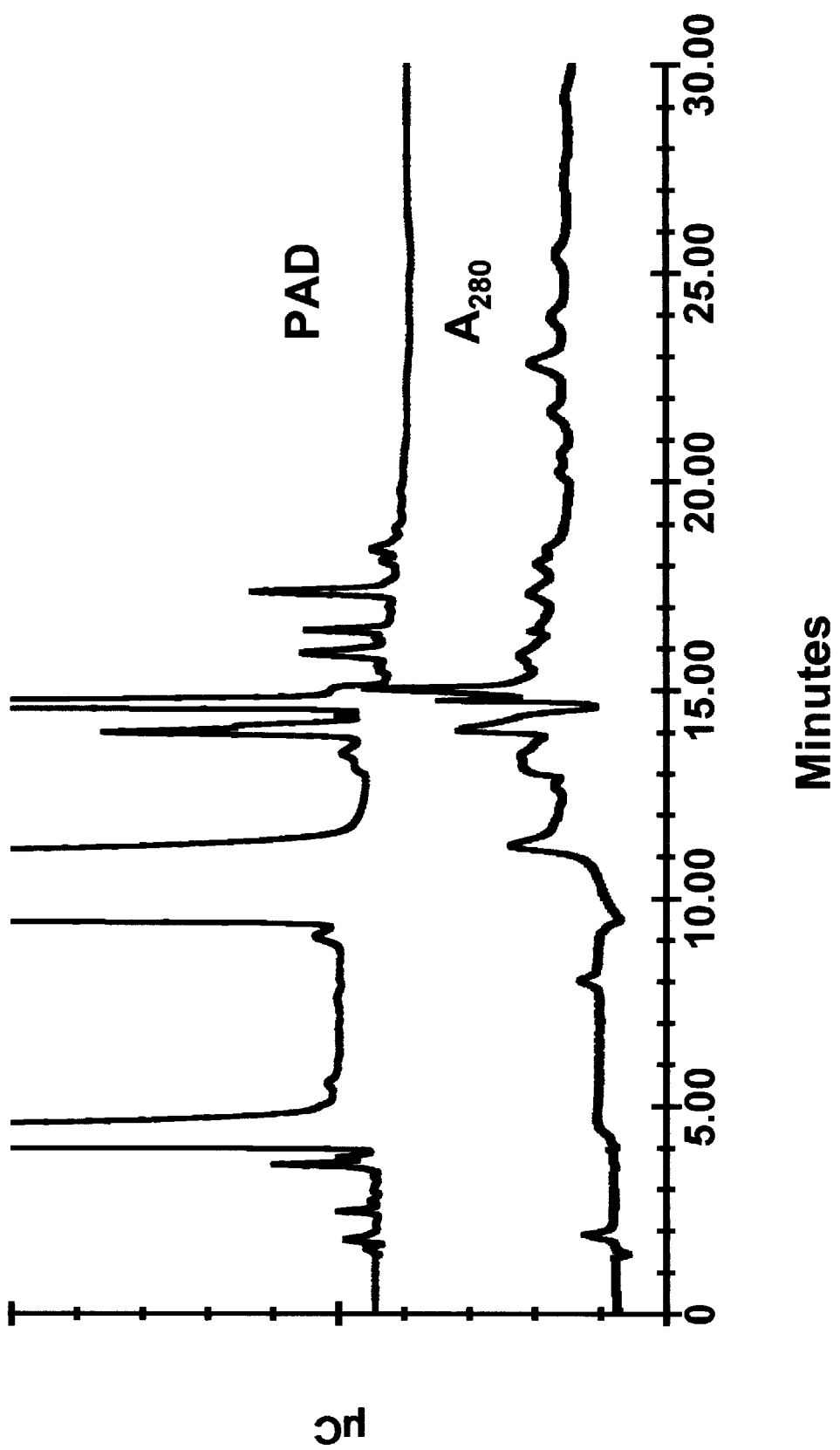
FIG. 27 shows the absorbance at 280 nm of carbohydrates released by chymotrypsin indicate the presence of a protein or glycoprotein.

The carbohydrate peaks released with retention times between 14 and 20 minutes also contain a constituent, which absorbs at 280 nm as shown in FIG. 27. The absorbance at 280 nm is usually due to the phenolic amino acids phenylalanine and tyrosine in proteins although other compounds may also absorb at 280 nm. Based on this result along with the material released by the proteases, it is concluded that the carbohydrate peaks in this 14–20 min range are glycoproteins. The observation that linking with a carbodiimide renders these carbohydrates more resistant to the protease release further substantiates the conclusion that they are, in fact, glycopeptides. The discovery that the protease digestion significantly increases the release of glucose and cellobiose confirms that the cellulosic constituents of the wall are cross-linked by a protease sensitive component (i.e., a protein or glycoprotein).

Figure 28:
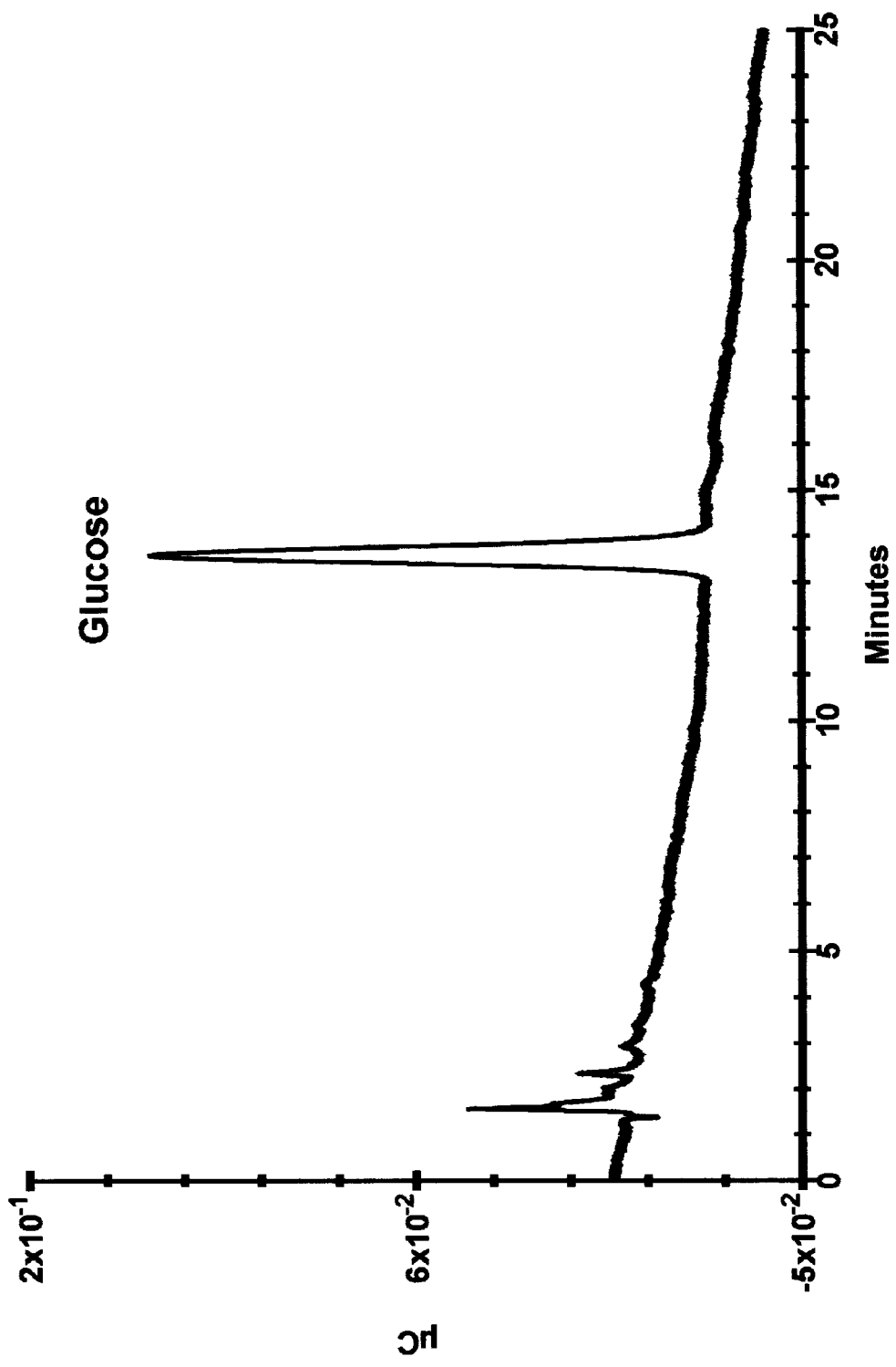
FIG. 28 shows the hydrolysis products of the white particle (presumably cellulose) left following the enzymatic digestions of FIGS. 23–26 and subsequent hydrolysis with 0.1N HCl for 30 min and 2N Trifluoroacetic Acid for 2 hr at 100° C.

The white rod-like particles released by the enzymatic degradation of the fibers were subjected to further purification. They were treated with 0.1N HCl for 30 min in a boiling water bath, which failed to solubilize them. The residue was also not soluble in 2N trichloroacetic acid at 100° C. for 2 hr but was completely dissolved by treatment with 6N HCl at 100° C. for 2 hr. The 6N HCl hydrolyzate was then chromatographed under conditions, of 15 mM NaOH, which resolves monosaccharides. The result is shown in FIG. 28, which shows a single peak with a retention time identical to that of glucose. At this time it appears that the white particles are essentially pure cellulose and yield only glucose upon hydrolysis in 6N HCl.

As detailed above, I have been able to obtain the multimers from a large molecular complex that is secreted by fibers, in vitro, by a temperature dependent mechanism. The relative distribution of the multimers can vary depending on the exogenous substrates incubated with the fibers and on the time of day that the bolls were collected. Under optimal conditions I have demonstrated the presence of the multimers in an initial soluble fraction, a secreted fraction which will not pass through a 0.2 $\mu$m filter, the precipitate of the aqueous extract and the fibers themselves. The multimers appear to play a structural role in the integrity of the cotton fiber since experiments to extract the multimers using specific enzymes resulted in a striking loss of the physical integrity of the cotton fibers.

The experiments just described demonstrate the $A_{280}$, profile of the material released by the sequential treatment of mature cotton fibers with ceilulase, chymotrypsin, cellulase and then chymotrypsin again. These profiles indicate that the multimers are probably attached to protein. When the fibers are treated with a water-soluble carbodiimide to form amide bonds between the carboxyl and amino groups of the amino acid constituents, the fibers become more resistant to enzymatic degradation. This result shows that bifunctional reagents have applications in the textiles and lead to ways to improve the quality (e.g., durability) of cotton fabric. I have shown that normal cotton textiles continually shed water-soluble multimers over the life of the fabric. This suggests that fabric wear is at least partially due to loss of soluble material during washing. Chemical cross-linking is a way to reduce this loss and, thereby, extend the life of cotton fabrics. Although this test employed carbodiimide any of a large number of bifunctional reagents known to react with amino groups can be used. These reagents are well known to a person of ordinary skill in the art of protein chemistry. The significant point is that my experiment is the first demonstration that protein cross-inking reagents are useful to alter properties of cotton and other plant-based textiles.

Hydrolysis experiments on the white particulate material which remains following the enzymatic digestion of the fibers is consistent with these particles being perhaps very highly crystalline cellulose. This result is consistent with the prediction by Balls (1928) that the fiber wall is made up of little domino or brick-like structures which are held together and permit the fiber to be flexible. It is probable that the material that holds the "bricks" together is the "glue" matrix described in part here with the multimers attached to a protein backbone. This result is consistent with the fact that plant breeders directly select for varieties with different fiber properties including strength. It is likely that a matrix protein is a primary gene product while a polysaccharide, such as cellulose, is the product of a number of genes. Thus, direct selection and manipulation by genetic engineering should be more successful on the matrix protein than on the complex of enzymes needed to synthesize cellulose.

Source Identification of Woods and Other Plant Materials

The above-described experiments indicated that plant cell wall materials such as cotton would give surprisingly consistent patterns of extracted multimers. This suggested that the method might yield unique "fingerprints" that could be used for identifying the origin of cellulosic materials for forensic and other purposes (e.g., quality control of wood pulps, etc.). The present method of analysis has now been extended to a wide variety of cellulose containing materials (many of them exotic woods). My current working hypothesis is that cellulose is synthesized on a glycosylated protein template and the oligomers (multimers) released by the treatment with dilute HCl by boiling for 30 min are derived from this glycosylated protein template. Therefore, it is logical to assume that such oligomers will be released from virtually all cellulose containing materials which are derived from a plant cell wall, assuming that virtually all plant materials will contain templated polysaccharides that have not yet been tightly incorporated into the cell wall. Each species of plant would be expected to have slightly different enzymes and pool sizes of various cell wall precursors. This would lead to each type (species) of wood—essentially composed of secondary cell walls containing cellulose and lignin—having unique cellulose characteristics.

Figure 37:
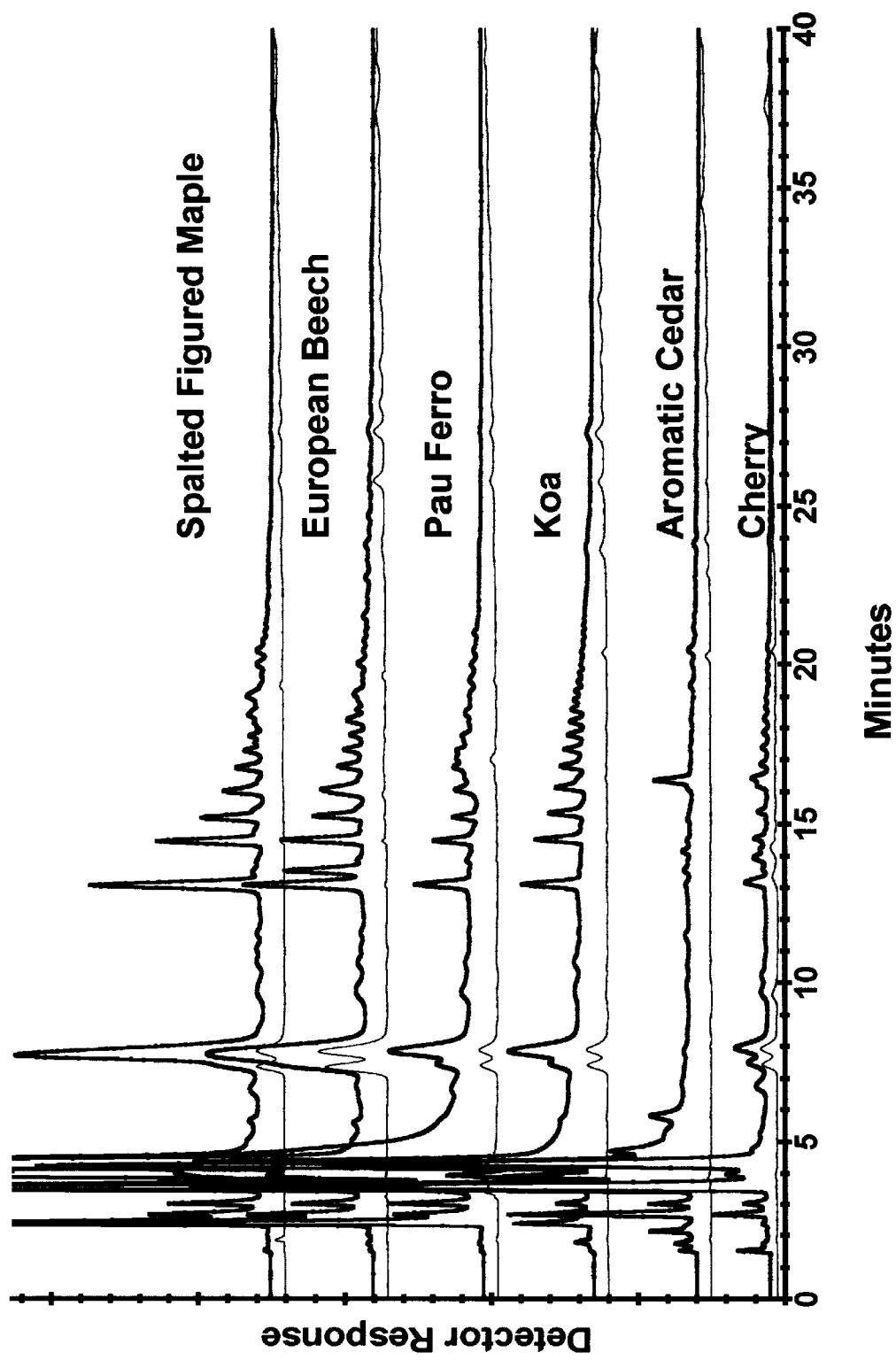
FIG. 37 shows the variations in multimer patterns extracted from different woods (in each instance the light trace shows the UV absorbance): a) spatted maple (Acer sp.); b) European beech (Fagus sp.); c) pau ferro; d) koa (Acacia sp.); e) aromatic cedar; f) cherry (Prunus sp.).
Figure 38:
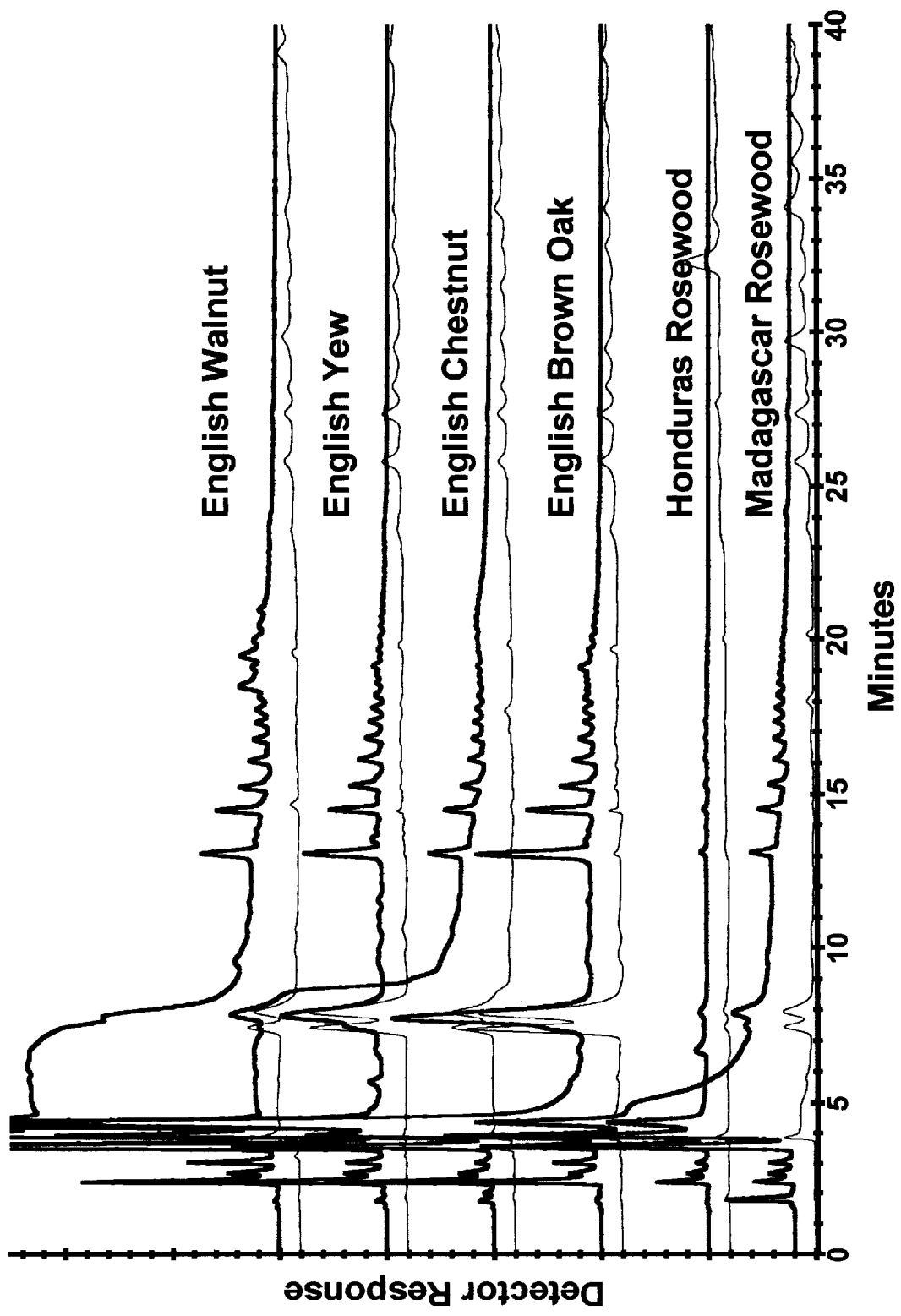
FIG. 38 shows the variations in multimer patterns extracted from different woods (in each instance the light trace shows the UV absorbance): a) English walnut (Juglans sp.); b) English yew (Taxus sp.); c) English chestnut (Castanea sp.); d) English brown oak (Quercus sp.); e) Hondurus rosewood; and f) Madagascar rosewood.
Figure 39:
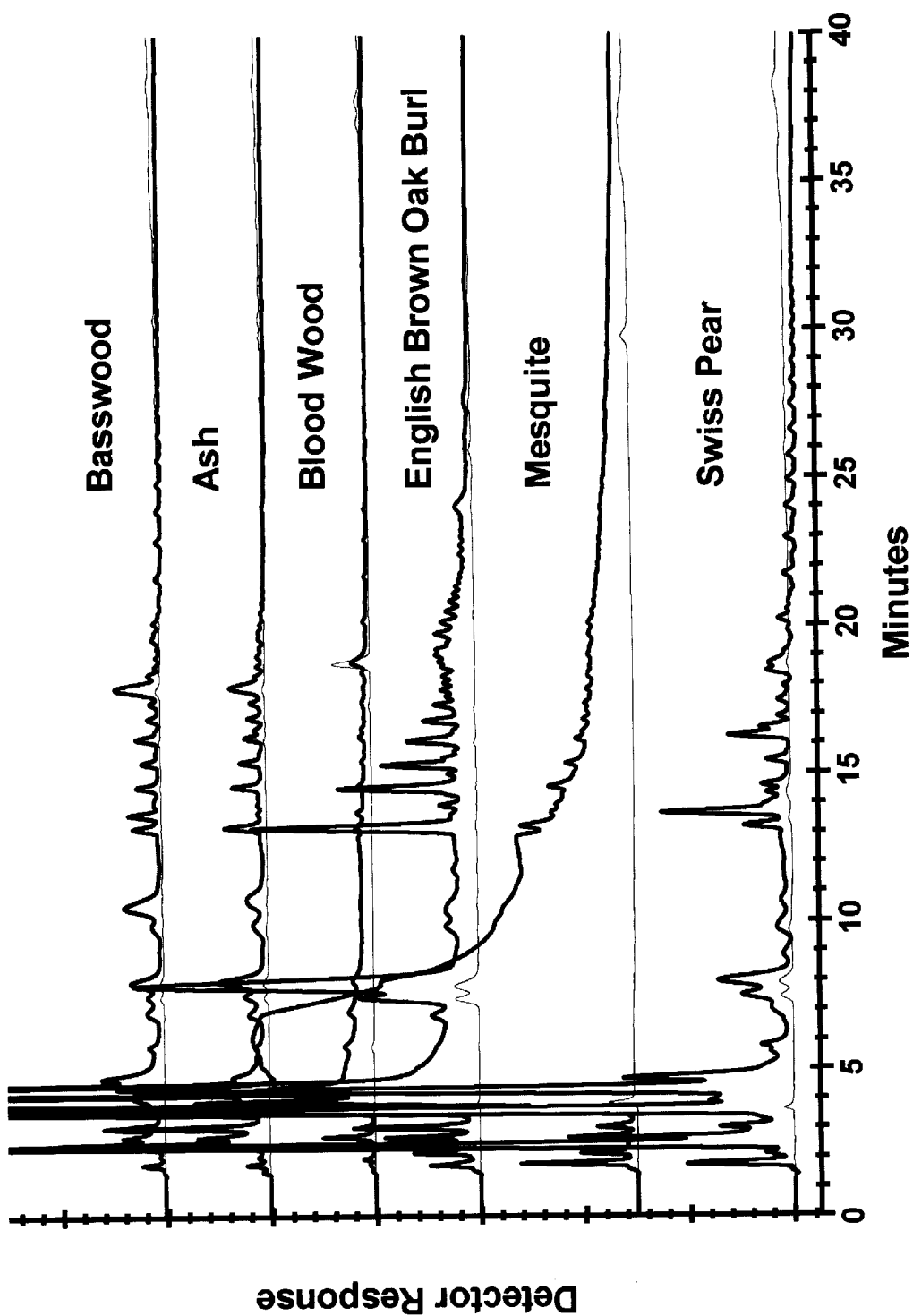
FIG. 39 shows the variations in multimer patterns extracted from different woods (in each instance the light trace shows the UV absorbance): a) basswood (Tilia sp.); b) ash (Fraxinus sp.); c) blood wood; d) English brown; e) mesquite (Proscopis sp.) and f) Swiss pear (Pyrus sp.).
Figure 40:
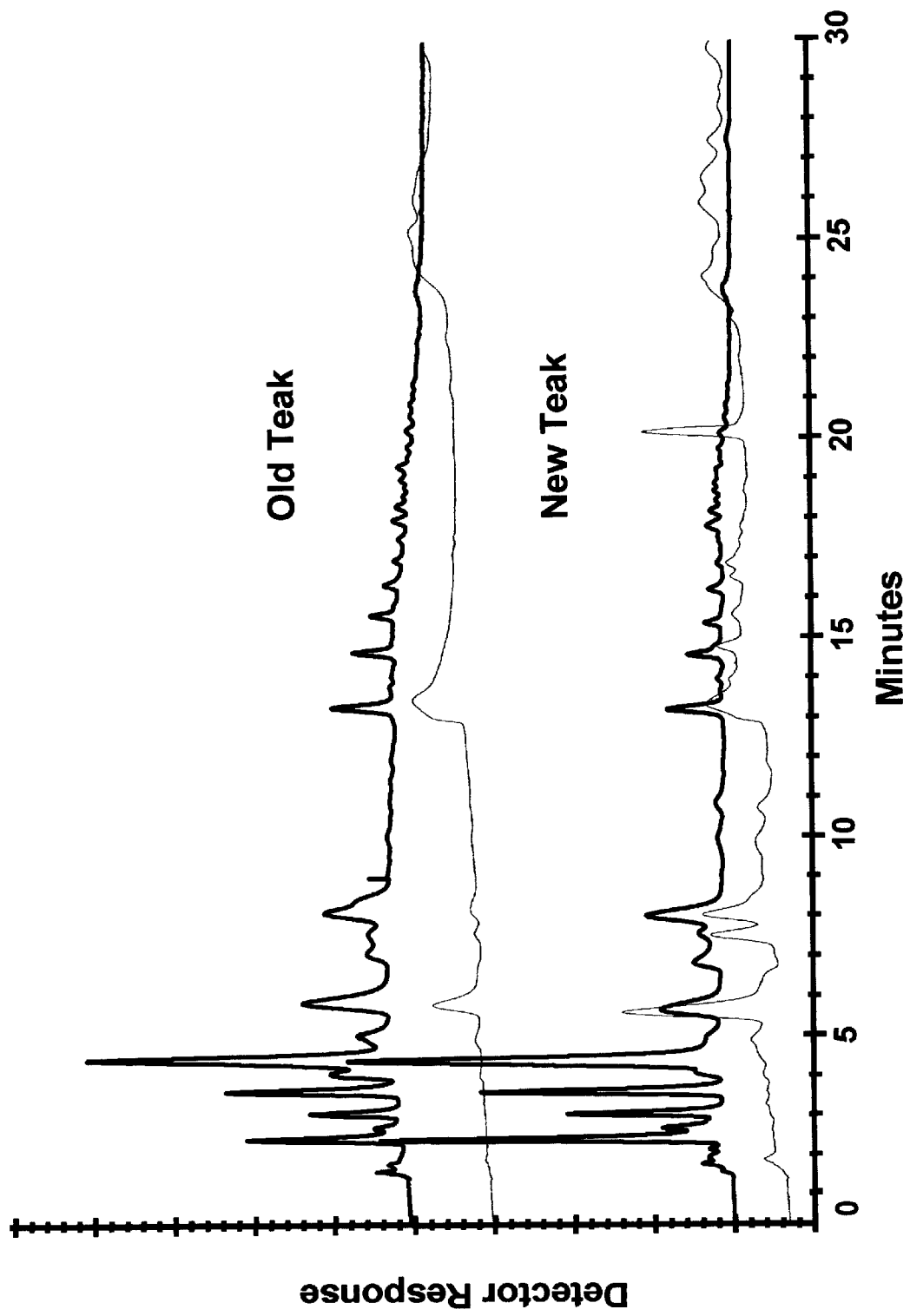
FIG. 40 shows the variations in multimer patterns extracted from old and new teak (in each instance the light trace shows the UV absorbance): a) old teak removed from a boat deck after 19 years service—scale expanded 10x; b) new teak-scale not expanded.
Figure 41:
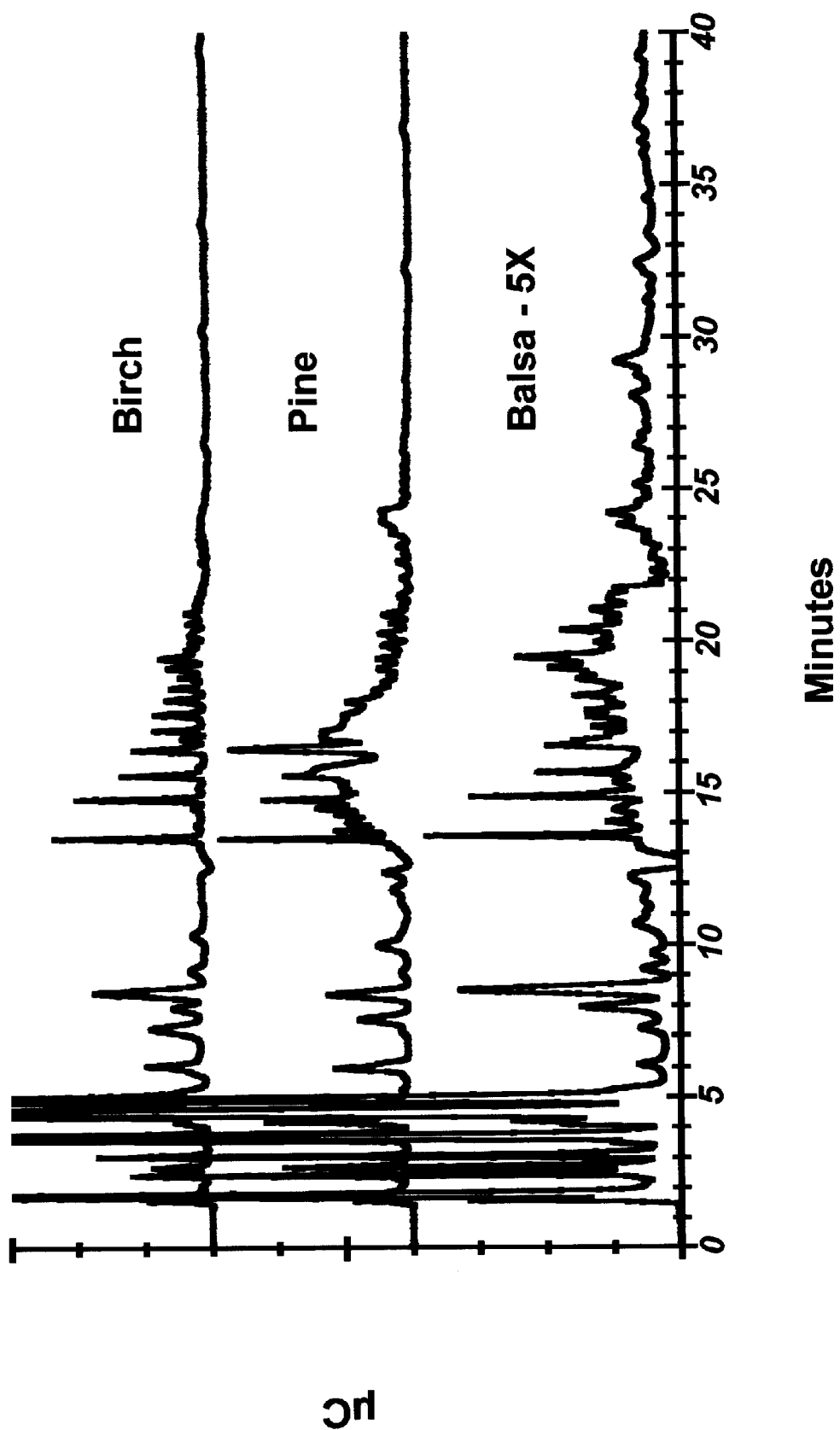
FIG. 41 shows the variation in multimer patterns extracted from (a) birch, (b) pine and (c) balsa (the balsa scale is expanded 5X).

A survey of several kinds of wood has been performed with the method of the present invention The results of this survey are show in FIGS. 37–39. To date the following kinds of wood have been analyzed: birch, pine, balsa, basswood, ash, English brown oak, mesquite, Swiss pear, English walnut, English yew, English chestnut, English brown oak burl, Honduras rosewood, Madagascar rosewood, spalted figured maple, European beech, pau ferro, koa, aromatic cedar, cherry as well as both new teak and old weathered teak (FIG. 40). In all cases each species of wood has a unique "signature" or "fingerprint". Some are very similar such as pau ferro and ironwood, but when the chromatograms are closely compared one can distinguish unique species specific differences. Difference in the "fingerprints" can be readily seen in FIG. 41 which shows extracts from less exotic woods, namely birch, pine and balsa. Birch and pine vary particularly in the peaks between 15 and 20 minutes retention. Balsa has a lower level of multimers and is presented on a five-fold expanded scale. The measurement of UV absorbance at 280 nm adds an additional dimension. This absorbance reflects the presence of phenolic compounds and could represent phenolic amino acids in proteins, but it also can be the result of other phenolic compounds such as the constituents of lignin in wood. In the case of teakwood, new wood was compared with old teak, which had been removed from the deck of a boat after being exposed to weather and the elements for 19 years. The UV absorbing compounds are almost completely gone from the old teak while the new teak has them in abundance. The chromatogram of the dilute acid extracted oligomers of the old teak is essentially identical to that of the new teak when the scale is amplified 20×for purposes of comparison. This is probably the result of much of the oligomeric material being extracted by repeated exposure to both salt and fresh water as well as exposure to sunlight.

Figure 29:
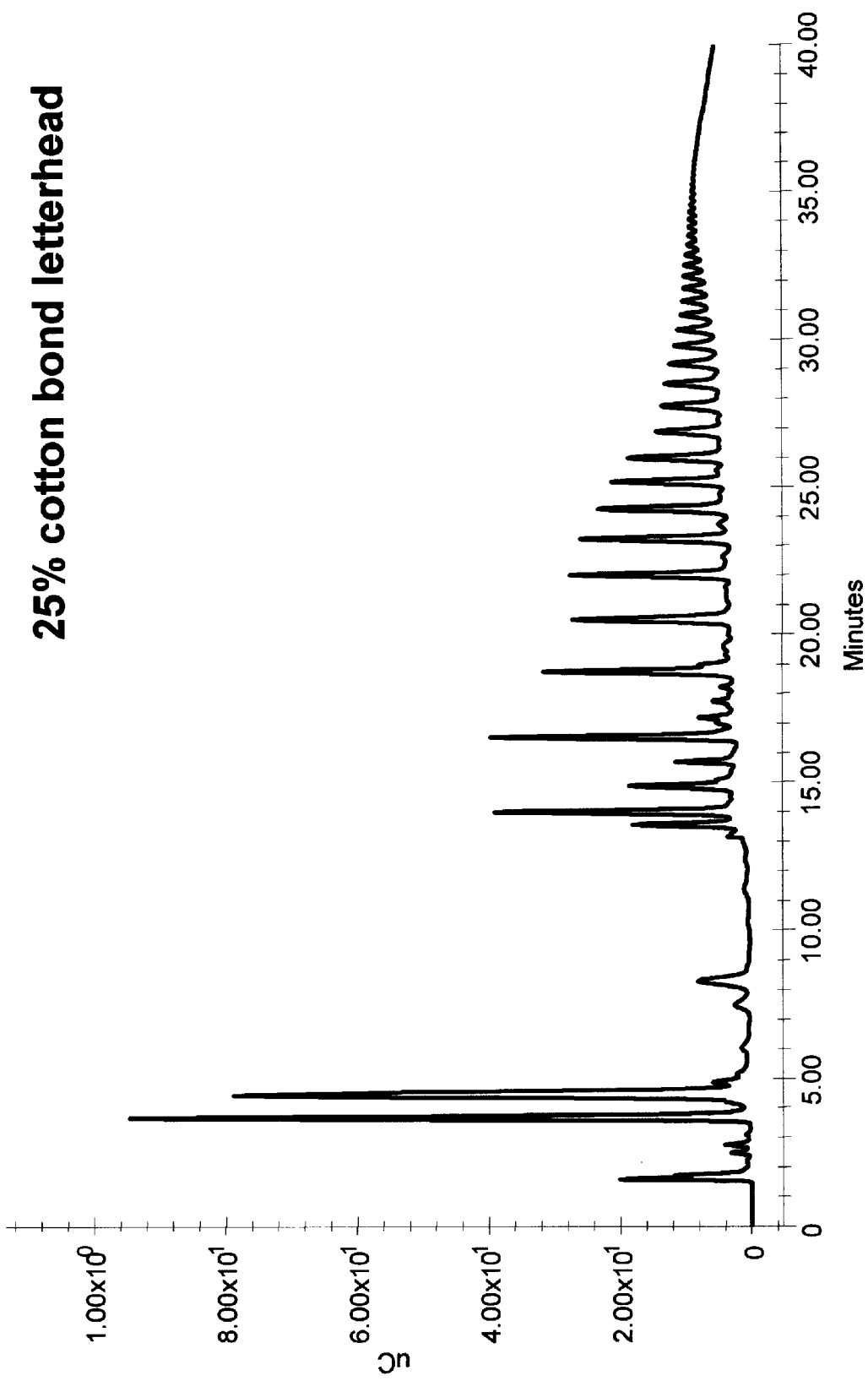
FIG. 29 shows multimers extracted from 25% cotton bond paper.
Figure 30:
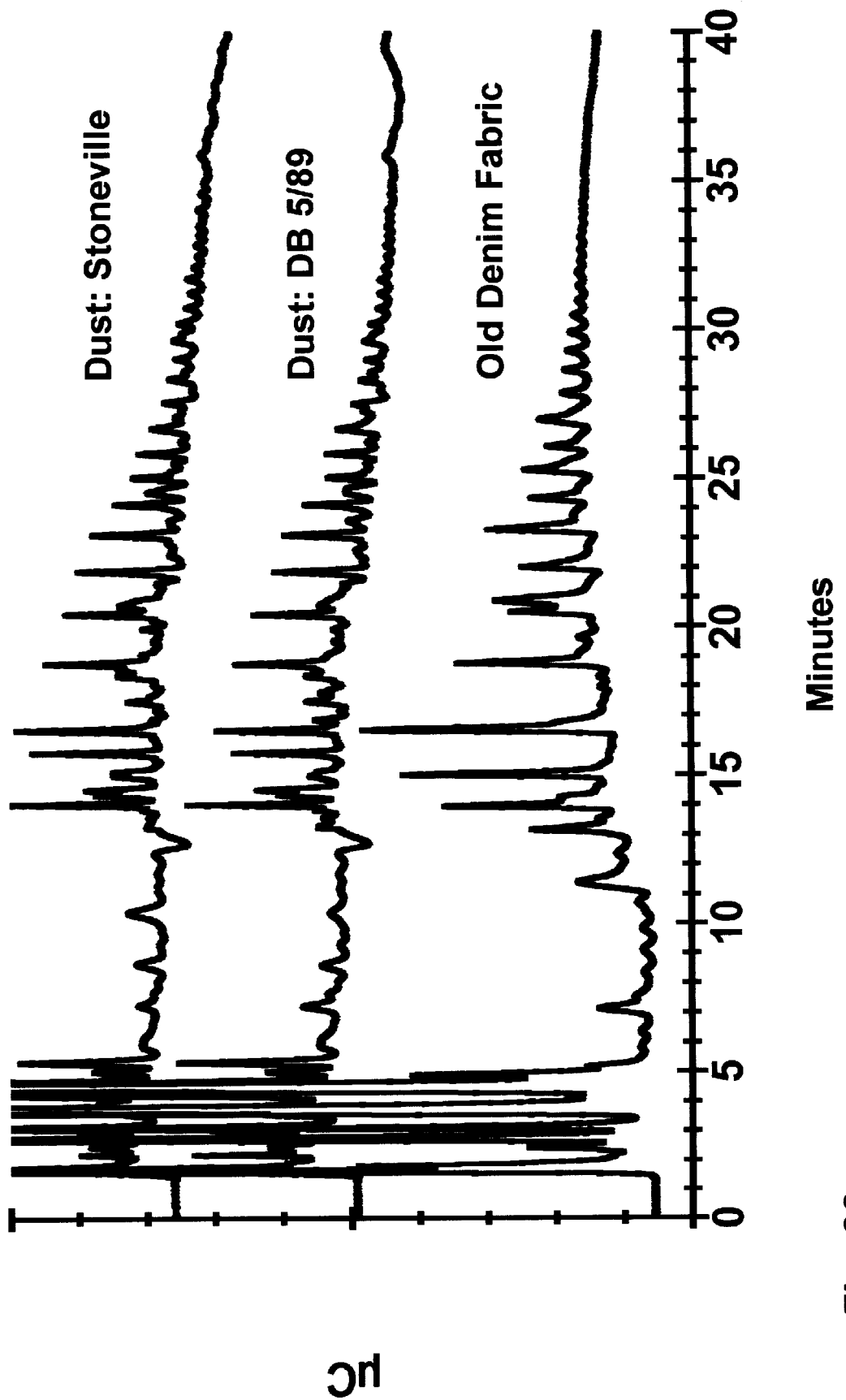
FIG. 30 shows the multimners extracted from cotton dust and from old denim fabric.
Figure 35:
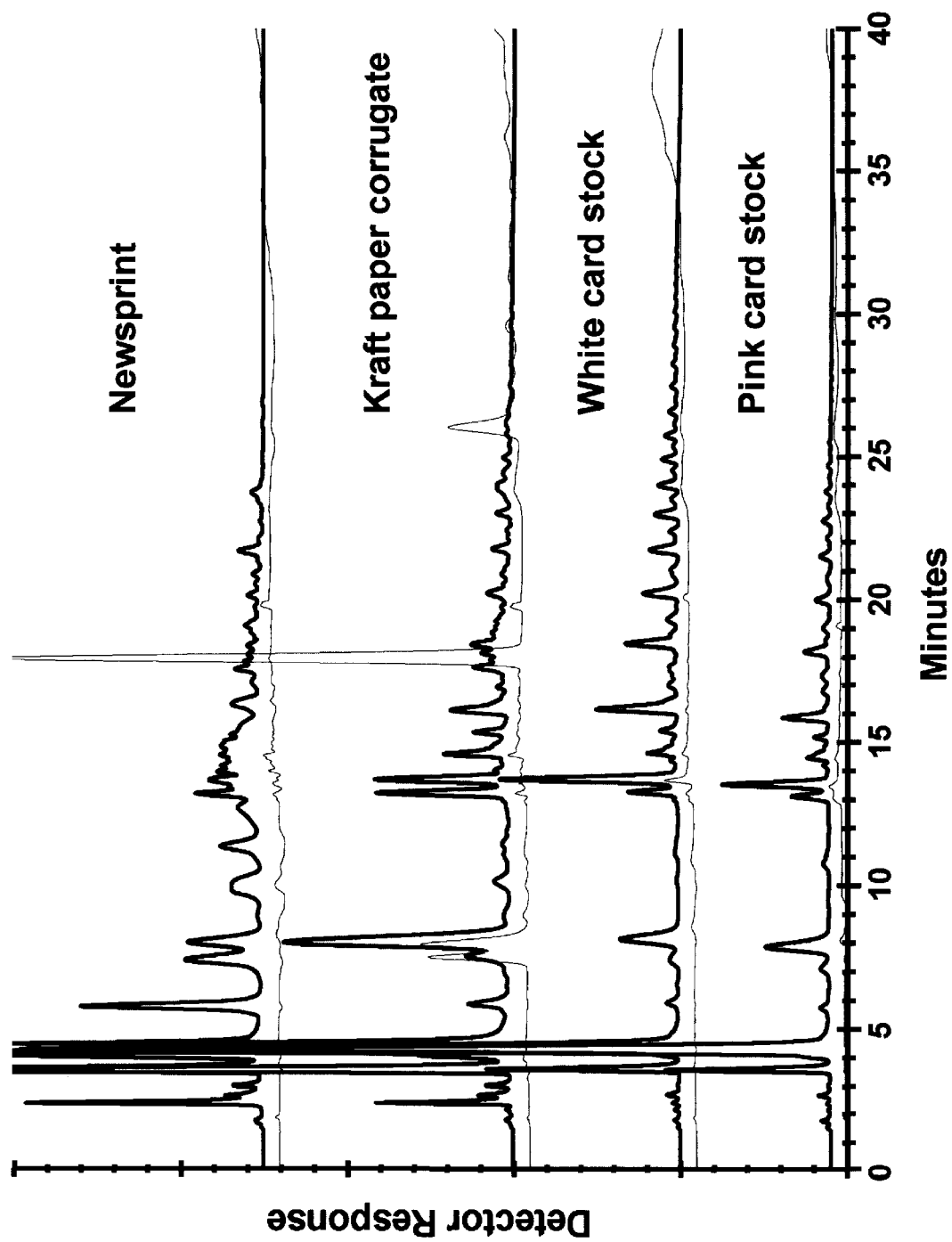
FIG. 35 shows multimers extracted from various paper products (matched on a weight basis): a) newsprint (light trace shows UV absorbance); b) Kraft paper corrugate (light trace shows UV absorbance—probably lignin); c) white card stock (light trace shows UV absorbance); and d) pink card stock (light trace shows UV absorbance.
Figure 36:
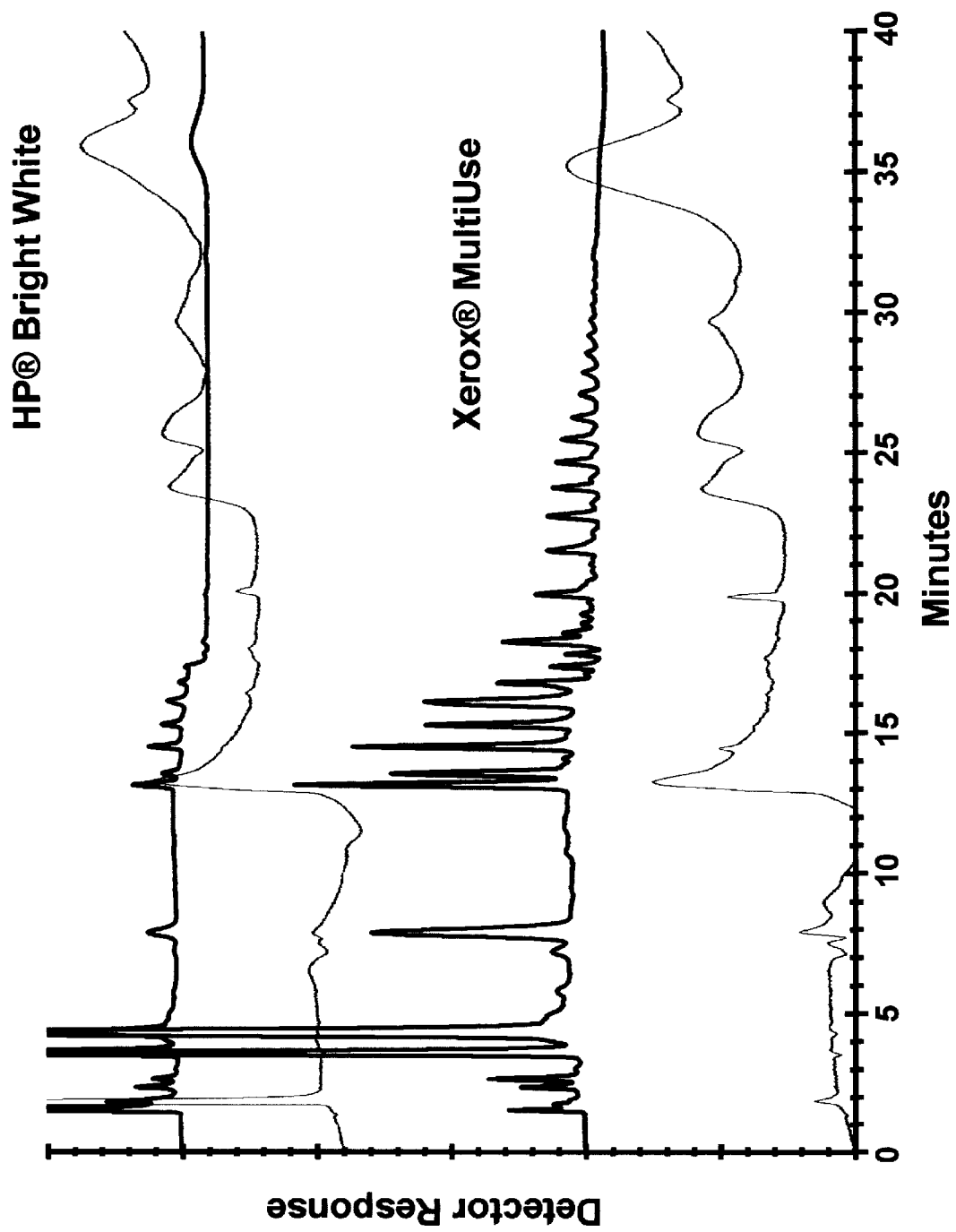
FIG. 36 shows a comparison (matched on a weight basis) of multimers extracted from two grades of "white" paper: a) shows a high purity bright white paper that shows relatively few multimers (light trace is UV absorbance; b) shows a lower grade "copy" paper with a larger number of multimers (light trace is UV absorbance); the UV traces may be due in part to "optical brighteners" in the paper.

The method of the present invention has also been extended to pulp and paper products since they are derived from wood pulp. FIGS. 29, and 35–36 show the analyses of the following paper products: 25% cotton bond letterhead, newsprint, cardboard shipping box, a pink index card, white index card, catalogue paper, poster board, Xerox® MultiUse primary image paper and Hewlett-Packardo bright white inkjet paper. Again, it is evident that each type of paper product has a unique signature or "fingerprint" which probably reflects the degree of processing. The most highly processed of the papers investigated appears to be the bright white inkjet paper (FIG. 36a) which shows the lowest abundance and distribution of the acid labile multimers. It is reasonable to assume that this paper has gone through more extensive washing and bleaching than the other papers analyzed.

The present invention would appear to be a more quantitative and automatic replacement for the "classical" microscopic approach of identifying wood samples. Previously a plant anatomist with considerable expertise was needed to identify small wood samples by examining microscopic cellular structures. There are a number of reasons that identification of wood samples might be required. In the case of imported wood products it might be required to demonstrate that none of the wood comes from endangered species. Some exotic wood is extremely expensive. Proof might be required that the wood is indeed of the correct, rare species. The present invention is also a quality control method for wood pulp processing. The type and quantity of multimers correlates with the degree of processing of wood pulp with the purer, higher quality pulps resulting from more extensive processing. The present method allows a given pulp sample to be rapidly and unambiguously evaluated to demonstrate pulp quality.

In addition to the equivalents of the claimed elements, obvious substitutions known to one with ordinary skill in the art are defined to be within the scope of the defined elements. Those skilled in the art will appreciate that various adaptations and modifications of the just-described preferred embodiment can be configured without departing from the scope and spirit of the invention. The illustrated embodiment has been set forth only for the purposes of example and that should not be taken as limiting the invention. Therefore, it is to be understood that, within the scope of the appended claims, the invention may be practiced other than as specifically described herein.

I claim:

1. A method of analyzing textiles, wood pulp and cellulosic materials comprising the steps of:

making a cold aqueous extraction of a sample selected from the group consisting of textile, wood pulp and cellulosic material;

reserving the extracted sample;

extracting the extracted sample with dilute hot acid to produce an extract; and analyzing the extract to reveal a pattern of carbohydrate multimers, wherein the pattern of the carbohydrate multimers is indicative of a characteristic of the sample.

2. The method of claim 1, wherein heavily laundered textile samples are distinguished from less heavily laundered textile samples by a showing of fewer carbohydrate multimers when the extract is analyzed.

3. The method of claim 1, wherein highly processed wood pulp is distinguished from less highly processed wood pulp by a showing of fewer carbohydrate multimers when the extract is analyzed.

4. A method of analyzing cotton textiles to predict the presence of abnormal cotton fibers that have abnormal dyeing properties, the method comprising:

making a cold aqueous extraction of a series of cotton textile samples;

reserving the extracted cotton textile samples;

extracting the extracted cotton textile samples with dilute hot acid to produce acid extracts;

analyzing the acid extracts to reveal patterns of carbohydrate multimers; and determining which extracts have multimers containing a higher ratio of arabinose to glucose, which higher ratio indicates the presence of abnormal cotton fibers.

5. A method to identify the species of a sample of word or other cellulosic material comprising the steps of:

making a cold aqueous extraction of specimens of known species of wood or cellulosic material;

reserving the extracted specimens;

extracting the extracted specimens with dilute hot acid to produce known extracts;

analyzing each known extract to reveal a pattern of carbohydrate multimers characteristic of the species from which the extract was made;

making a cold aqueous extraction of the sample of wood or cellulosic material;

reserving the extracted sample; extracting the extracted sample with dilute hot acid to produce a sample extract;

analyzing the sample extract to reveal a pattern of carbohydrate multimers characteristic of the sample extract; and comparing the pattern of the sample extract to the patterns of the known extracts, wherein the species of the sample is determined when the pattern of the sample extract matches the pattern of a known extract.

* * * * *